US010201329B2

United States Patent
Ichikawa

(10) Patent No.: US 10,201,329 B2
(45) Date of Patent: *Feb. 12, 2019

(54) ULTRASOUND OBSERVATION APPARATUS, METHOD FOR OPERATING ULTRASOUND OBSERVATION APPARATUS, AND COMPUTER-READABLE RECORDING MEDIUM

(71) Applicant: OLYMPUS CORPORATION, Tokyo (JP)

(72) Inventor: Junichi Ichikawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/255,246

(22) Filed: Sep. 2, 2016

(65) Prior Publication Data

US 2016/0367225 A1 Dec. 22, 2016

Related U.S. Application Data

(63) Continuation of application No. PCT/JP2015/078534, filed on Oct. 7, 2015.

(30) Foreign Application Priority Data

Dec. 22, 2014 (JP) ................................. 2014-259471

(51) Int. Cl.
*A61B 8/08* (2006.01)
*A61B 8/00* (2006.01)
(Continued)

(52) U.S. Cl.
CPC .............. *A61B 8/5269* (2013.01); *A61B 8/14* (2013.01); *A61B 8/461* (2013.01); *A61B 8/469* (2013.01);
(Continued)

(58) Field of Classification Search
CPC ............ G01S 7/52033; G01S 7/52098; G01S 7/52036; G01S 7/52; G01S 7/52071;
(Continued)

(56) References Cited

U.S. PATENT DOCUMENTS 8,917,919 B2  12/2014  Noguchi
2012/0310087 A1  12/2012  Miyaki et al.
(Continued)

FOREIGN PATENT DOCUMENTS

CN  103200876 A  7/2013
JP  2010-051553 A  3/2010
(Continued)

OTHER PUBLICATIONS

International Search Report dated Jan. 12, 2016 issued in PCT/JP2015/078534.
(Continued)

*Primary Examiner* — Elmer Chao
(74) *Attorney, Agent, or Firm* — Scully, Scott, Murphy & Presser, P.C.

(57) ABSTRACT

An ultrasound observation apparatus includes: a frequency analysis unit that analyzes a frequency of the ultrasound signal to calculate frequency spectra according to a reception depth and a reception direction of the ultrasound signal; an optimal attenuation rate setting unit configured to: calculate features of the frequency spectra; perform attenuation correction on the features of the frequency spectra for eliminating influence of attenuation of the ultrasound wave, using attenuation rate candidate values providing different attenuation characteristics which are attenuation characteristics in propagating the ultrasound wave through the observation target, thereby to calculate corrected features of the frequency spectra for each of the attenuation rate candidate values; and set an optimal attenuation rate to the observation
(Continued)

target from among the attenuation rate candidate values, based on the corrected features; and an attenuation rate image data generation unit that generates attenuation rate image data for displaying information on the optimal attenuation rate.

10 Claims, 15 Drawing Sheets

(51) Int. Cl.
*G01S 7/52* (2006.01)
*A61B 8/14* (2006.01)
*A61B 8/12* (2006.01)

(52) U.S. Cl.
CPC ........ *A61B 8/5207* (2013.01); *G01S 7/52033* (2013.01); *G01S 7/52036* (2013.01); *G01S 7/52071* (2013.01); *A61B 8/12* (2013.01)

(58) Field of Classification Search
CPC ... A61B 8/5207; A61B 8/5223; A61B 8/5292; A61B 8/08; A61B 8/485; A61B 8/5269; A61B 8/461; A61B 8/469; A61B 8/12; A61B 8/14; A61B 8/4444; A61B 8/4483
See application file for complete search history.

(56) References Cited

U.S. PATENT DOCUMENTS

| | | |
|---|---|---|
| 2013/0035594 A1 | 2/2013 | Eda |
| 2013/0109968 A1 | 5/2013 | Azuma |
| 2014/0309531 A1 | 10/2014 | Eda |

FOREIGN PATENT DOCUMENTS

| | | |
|---|---|---|
| WO | 2007/003058 A1 | 1/2007 |
| WO | 2012/063976 A1 | 5/2012 |
| WO | WO 2013/179859 A1 | 12/2013 |
| WO | 2014/054469 A1 | 4/2014 |

OTHER PUBLICATIONS

Extended Supplementary European Search Report dated Aug. 7, 2018 in European Patent Application No. 15 87 2416.1.
Chinese Office Action dated Aug. 30, 2018 in Chinese Patent Application No. 201580012094.7.

ULTRASOUND OBSERVATION APPARATUS, METHOD FOR OPERATING ULTRASOUND OBSERVATION APPARATUS, AND COMPUTER-READABLE RECORDING MEDIUM

CROSS REFERENCES TO RELATED APPLICATIONS

This application is a continuation of PCT international application Ser. No. PCT/JP2015/078534, filed on Oct. 7, 2015 which designates the United States, incorporated herein by reference, and which claims the benefit of priority from Japanese Patent Application No. 2014-259471, filed on Dec. 22, 2014, incorporated herein by reference.

BACKGROUND

1. Technical Field

The disclosure relates to an ultrasound observation apparatus for observing tissue to be observed using ultrasound waves, a method for operating the ultrasound observation apparatus, and a computer-readable recording medium.

2. Related Art

Conventionally, for an ultrasound observation apparatus for observing tissue to be observed with the use of ultrasound waves, various attempts have been made to accurately estimate characteristics of tissue to be observed using ultrasound attenuation characteristics. For example, a technique for displaying hue information to be superimposed on tomographic image data is known. In the technique, intensity change rates (attenuation characteristics) are calculated in a small interval in a depth direction of a living body for reception signals of ultrasound signals having different frequencies, the intensity change rates are compared with one another to add hue information according to the characteristics of tissue at each point on a tomographic image, and the hue information is displayed to be superimposed on the tomographic image data (e.g., see JP 2010-51553 A).

SUMMARY

In some embodiments, provided is an ultrasound observation apparatus for generating an ultrasound image based on an ultrasound signal obtained by an ultrasound probe having an ultrasound transducer that is configured to transmit an ultrasound wave to an observation target and to receive the ultrasound wave reflected from the observation target. The ultrasound observation apparatus includes: a frequency analysis unit configured to analyze a frequency of the ultrasound signal to calculate a plurality of frequency spectra according to a reception depth and a reception direction of the ultrasound signal; an optimal attenuation rate setting unit configured to: calculate features of the plurality of frequency spectra; perform attenuation correction on the features of the frequency spectra for eliminating influence of attenuation of the ultrasound wave, using a plurality of attenuation rate candidate values providing different attenuation characteristics which are attenuation characteristics in propagating the ultrasound wave through the observation target, thereby to calculate corrected features of the frequency spectra for each of the attenuation rate candidate values; and set an optimal attenuation rate to the observation target from among the plurality of attenuation rate candidate values, based on a calculation result of the corrected features; and an attenuation rate image data generation unit configured to generate attenuation rate image data for displaying information on the optimal attenuation rate.

In some embodiments, a method for operating an ultrasound observation apparatus is provided. The ultrasound observation apparatus generates an ultrasound image based on an ultrasound signal obtained by an ultrasound probe having an ultrasound transducer that is configured to transmit an ultrasound wave to an observation target and to receive the ultrasound wave reflected from the observation target. The method includes: analyzing, by a frequency analysis unit, a frequency of the ultrasound signal to calculate a plurality of frequency spectra according to a scanning position of the ultrasound transducer; calculating, by an optimal attenuation rate setting unit, features of the plurality of frequency spectra, performing attenuation correction on the features of the frequency spectra for eliminating influence of attenuation of the ultrasound wave by using a plurality of attenuation rate candidate values providing different attenuation characteristics which are attenuation characteristics in propagating the ultrasound wave through the observation target, thereby to calculate corrected features of the frequency spectra for each of the attenuation rate candidate values, and setting an optimal attenuation rate to the observation target from among the plurality of attenuation rate candidate values based on a calculation result of the corrected features; and generating, by an attenuation rate image data generation unit, attenuation rate image data for displaying information on the optimal attenuation rate.

In some embodiments, a non-transitory computer-readable recording medium with an executable program stored thereon is provided. The program causes an ultrasound observation apparatus that generates an ultrasound image based on an ultrasound signal obtained by an ultrasound probe having an ultrasound transducer that is configured to transmit an ultrasound wave to an observation target and to receive the ultrasound wave reflected from the observation target, to execute: analyzing, by a frequency analysis unit, a frequency of the ultrasound signal to calculate a plurality of frequency spectra according to a scanning position of the ultrasound transducer; calculating, by an optimal attenuation rate setting unit, features of the plurality of frequency spectra, performing attenuation correction on the features of the frequency spectra for eliminating influence of attenuation of the ultrasound wave by using a plurality of attenuation rate candidate values providing different attenuation characteristics which are attenuation characteristics in propagating the ultrasound wave through the observation target, thereby to calculate corrected features of the frequency spectra for each of the attenuation rate candidate values, and setting an optimal attenuation rate to the observation target from among the plurality of attenuation rate candidate values based on a calculation result of the corrected features; and generating, by an attenuation rate image data generation unit, attenuation rate image data for displaying information on the optimal attenuation rate.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the present invention (hereinafter referred to as "embodiment(s)") will be described below with reference to the accompanying drawings.

First Embodiment

Figure 1:
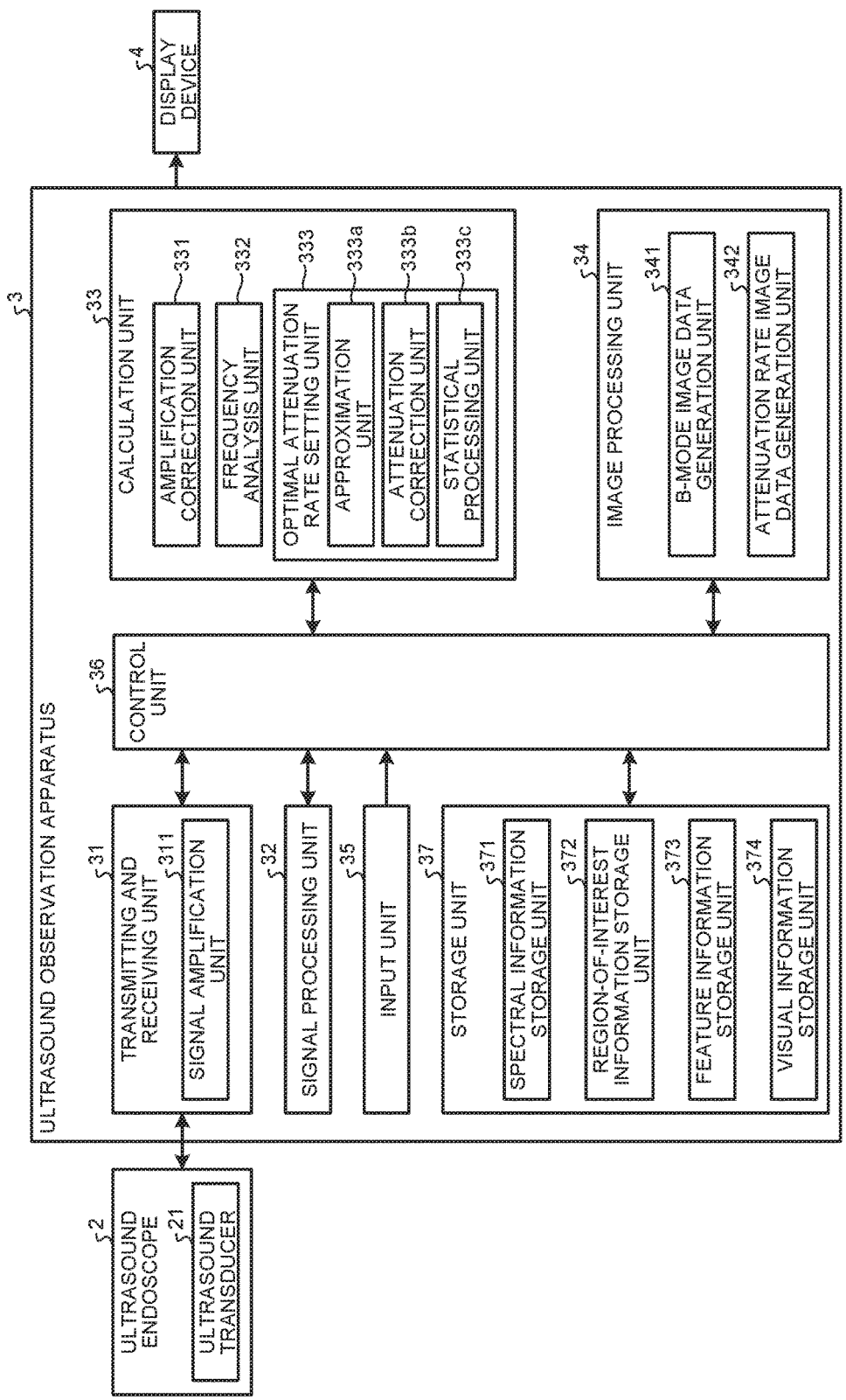
FIG. 1 is a block diagram illustrating a functional configuration of an ultrasound diagnostic system including an ultrasound observation apparatus according to a first embodiment of the present invention.

FIG. 1 is a block diagram illustrating a functional configuration of an ultrasound diagnostic system including an ultrasound observation apparatus according to a first embodiment of the present invention. An ultrasound diagnostic system 1 illustrated in FIG. 1 includes an ultrasound endoscope 2, an ultrasound observation apparatus 3, and a display device 4. The ultrasound endoscope 2 transmits an ultrasound wave to a subject as an observation target, and receives an ultrasound wave reflected from the subject, the ultrasound observation apparatus 3 generates an ultrasound image based on an ultrasound signal acquired by the ultrasound endoscope 2, and the display device 4 displays the ultrasound image generated by the ultrasound observation apparatus 3.

The ultrasound endoscope 2 has a distal end portion provided with an ultrasound transducer 21 for converting an electrical pulsed signal received from the ultrasound observation apparatus 3 to an ultrasound pulse (acoustic pulse) to irradiate the subject, converting ultrasound echo reflected from the subject to an electrical echo signal indicating voltage change, and outputting the echo signal. The ultrasound transducer 21 may employ any of a convex transducer, a linear transducer, and a radial transducer. The ultrasound endoscope 2 may cause the ultrasound transducer 21 to perform mechanical scanning, or may be provided with an array of elements as the ultrasound transducer 21 to electronically switch between elements relating to transmission and reception, or delay transmission and reception of each element, for electronic scanning.

The ultrasound endoscope 2 normally has an imaging optical system and an image sensor, is inserted into a subject's digestive tract (esophagus, stomach, duodenum, large intestine) or a subject's respiratory tract (trachea, bronchial tube), and images the digestive tract, the respiratory tract, or nearby organs (pancreas, gallbladder, bile duct, biliary tract, lymph node, mediastinal organs, blood vessel, or the like). The ultrasound endoscope 2 further has a light guide for introducing illumination light for irradiating the subject upon imaging. The light guide has a distal end portion reaching a distal end of an insertion section of the ultrasound endoscope 2 which is inserted into the subject, and a proximal end portion connected to a light source device for generating illumination light.

The ultrasound observation apparatus 3 includes a transmitting and receiving unit 31 electrically connected to the ultrasound endoscope 2, transmitting a transmission signal (pulsed signal) including a high-voltage pulse to the ultrasound transducer 21 based on a predetermined waveform and transmission timing, receiving an echo signal as an electrical reception signal from the ultrasound transducer 21 to generate digital radio frequency (RF) signal data (hereinafter, referred to as RF data) and output the data, a signal processing unit 32 for generating digital B-mode reception data based on the RF data received from the transmitting and receiving unit 31, a calculation unit 33 for performing predetermined calculation on the RF data received from the transmitting and receiving unit 31, an image processing unit 34 for generating various image data, an input unit 35 using a user interface such as a keyboard, a mouse, or a touch panel, and receiving input of various information, a control unit 36 for controlling the ultrasound diagnostic system 1 as a whole, and a storage unit 37 for storing various information required for operation of the ultrasound observation apparatus 3.

Figure 2:
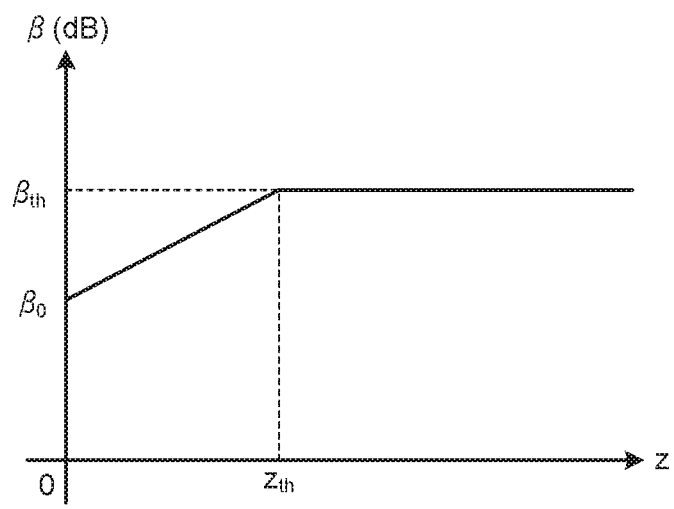
FIG. 2 is a graph illustrating a relationship between a reception depth and an amplification factor in amplification processing performed by a signal amplification unit of the ultrasound observation apparatus according to the first embodiment of the present invention.

The transmitting and receiving unit 31 has a signal amplification unit 311 for amplifying the echo signal. The signal amplification unit 311 performs sensitivity time control (STC) correction for amplifying an echo signal having a larger reception depth with a higher amplification factor. FIG. 2 is a graph illustrating a relationship between the reception depth and the amplification factor in amplification processing performed by the signal amplification unit 311. A reception depth z illustrated in FIG. 2 represents an amount of an ultrasound wave calculated based on time elapsed from reception start time of the ultrasound wave. As illustrated in FIG. 2, when the reception depth z is smaller than a threshold $z_{th}$, an amplification factor $\beta$ (dB) linearly increases from $\beta_0$ to $\beta_{th}$ ($>\beta_0$) with increase of the reception depth z. Furthermore, when the reception depth z is not less than the threshold $z_{th}$, the amplification factor $\beta$ (dB) takes a fixed value $\beta_{th}$. The threshold $z_{th}$ has a value representing that an ultrasound signal received from the observation target almost decays, and noise is dominantly generated. More generally, when the reception depth z is smaller than the threshold $z_{th}$, the amplification factor $\beta$ preferably monotonically increases with increase of the reception depth z. Note that, the relationship illustrated in FIG. 2 is previously stored in the storage unit 37.

The transmitting and receiving unit 31 performs processing such as filtering on the echo signal amplified by the signal amplification unit 311 and then performs A/D conversion to generate time domain RF data, and output the time domain RF data to the signal processing unit 32 and the calculation unit 33. Note that, when the ultrasound endoscope 2 is configured to cause the ultrasound transducer 21 provided with the array of elements to perform electronic scanning, the transmitting and receiving unit 31 has a multichannel circuit for beam synthesis corresponding to the elements.

A frequency range of the pulsed signal transmitted by the transmitting and receiving unit 31 is preferably a broadband substantially covering a linear response frequency range for electroacoustic conversion of the pulsed signal to the ultrasound pulse in the ultrasound transducer 21. The frequency range of various processing for the echo signal in the signal amplification unit 311 preferably is a broadband substantially covering the linear response frequency range for acoustic electrical conversion of the ultrasound echo to the echo signal performed by the ultrasound transducer 21. The above configuration allows accurate approximation during performance of approximation of a frequency spectrum described later.

The transmitting and receiving unit 31 also has functions of transmitting various control signals output from the control unit 36, to the ultrasound endoscope 2, and transmitting various information including identification ID, received from the ultrasound endoscope 2, to the control unit 36.

The signal processing unit 32 performs publicly known processing, such as use of bandpass filter, envelope detection, or logarithmic conversion on the RF data, and generates the digital B-mode reception data. In the logarithmic conversion, an amount obtained by dividing the RF data with a reference voltage $V_c$ is expressed in the form of common logarithm, and expressed as a decibel value. The signal processing unit 32 outputs the generated B-mode reception data, to the image processing unit 34. The signal processing unit 32 uses a central processing unit (CPU), various calculation circuit, or the like.

The calculation unit 33 has an amplification correction unit 331, a frequency analysis unit 332, and an optimal attenuation rate setting unit 333. The amplification correction unit 331 performs amplification correction on the RF data output from the transmitting and receiving unit 31 to have a constant amplification factor regardless of the reception depth thereof, the frequency analysis unit 332 performs fast Fourier transform (FFT) on the RF data subjected to the amplification correction for frequency analysis to calculate a plurality of frequency spectra according to a reception depth and a reception direction of an ultrasound signal, and the optimal attenuation rate setting unit 333 calculates features of the frequency spectra, performs attenuation correction for eliminating influence of ultrasound attenuation on the features of the frequency spectra (hereinafter, referred to as uncorrected features), using a plurality of attenuation rate candidate values providing different attenuation characteristics in propagating an ultrasound wave through the observation target, thereby to calculate corrected features of the frequency spectra for the attenuation rate candidate values, and sets an optimal attenuation rate suitable for the observation target from among the attenuation rate candidate values based on the calculation result. The calculation unit 33 uses a CPU, various calculation circuits, or the like.

Figure 3:
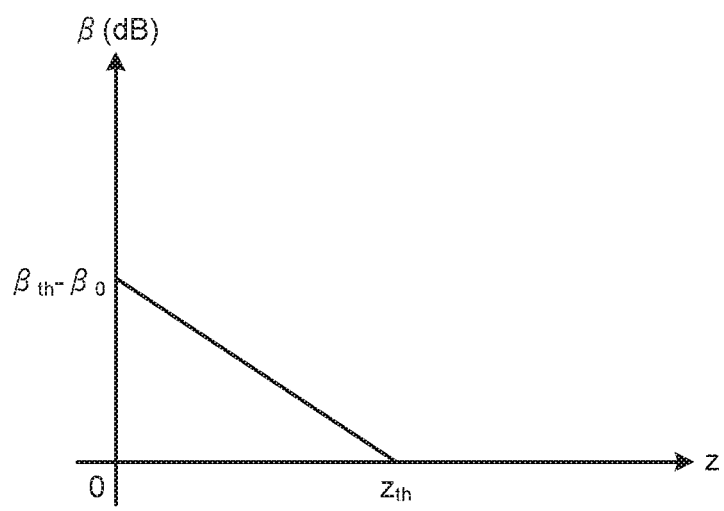
FIG. 3 is a graph illustrating a relationship between a reception depth and an amplification factor in amplification correction processing performed by an amplification correction unit of the ultrasound observation apparatus according to the first embodiment of the present invention.

FIG. 3 is a graph illustrating a relationship between the reception depth and the amplification factor in amplification correction processing performed by the amplification correction unit 331. As illustrated in FIG. 3, the amplification factor $\beta$ (dB) in the amplification processing performed by the amplification correction unit 331 takes a maximum value $\beta_{th}-\beta_0$ when the reception depth z is zero, linearly reduces when the reception depth z is zero to the threshold $z_{th}$, and reaches zero when the reception depth z is not less than the threshold $z_{th}$. Note that, the relationship illustrated in FIG. 3 is previously stored in the storage unit 37. The amplification correction unit 331 performs amplification correction on a digital RF signal based on the relationship illustrated in FIG. 3, cancels influence of the STC correction in the signal amplification unit 311, and outputs a signal having a constant amplification factor $\beta_{th}$. As a matter of course, the relationship between the reception depth z and the amplification factor $\beta$ in the amplification correction processing performed by the amplification correction unit 331 differs depending on the relationship between the reception depth and the amplification factor in the signal amplification unit 311.

A reason of such amplification correction will be described here. The STC correction is correction processing for eliminating influence of attenuation from an amplitude of an analog signal waveform. The STC correction amplifies the amplitude of the analog signal waveform uniformly over the whole frequency range, and amplifies the depth with a monotonically increasing amplification factor. Therefore, for generation of a B-mode image displaying amplitude of an echo signal converted to brightness, and scanning of homogeneous tissue, the STC correction is performed to make a luminance value constant regardless of depth. That is, the influence of attenuation is effectively removed from the luminance value of the B-mode image.

In contrast, when an analysis result of calculation of an ultrasound frequency spectrum is used, as described in the embodiment, even the STC correction cannot accurately eliminate the influence of attenuation caused by ultrasound transmission. This is because an attenuation amount generally differs depending on frequency (see formula (1) described later), but the STC correction has an amplification factor only changing depending on distance without frequency dependence.

In order to solve the above-mentioned problem, that is use of a result of calculation of the ultrasound frequency spectrum cannot accurately eliminate the influence of attenuation caused by ultrasound transmission, even using the STC correction, it may be conceivable to output a reception signal subjected to the STC correction upon generating a B-mode image, and perform new transmission different from transmission for generation of the B-mode image upon generating an image based on the frequency spectrum to output a reception signal not subjected to the STC correction. However, in this configuration, a frame rate of image data generated based on the reception signal is disadvantageously reduced.

Therefore, in the first embodiment, in order to eliminate influence of the STC correction from a signal subjected to the STC correction for a B-mode image, while maintaining a frame rate of image data to be generated, correction of the amplification factor is performed by the amplification correction unit 331.

The frequency analysis unit 332 samples RF data (line data) of each sound ray subjected to amplification correction by the amplification correction unit 331, at predetermined time intervals, and generates sample data. The frequency analysis unit 332 performs FFT processing on a sample data group to calculate a frequency spectrum at a plurality of locations (data positions) on the RF data.

Figure 4:
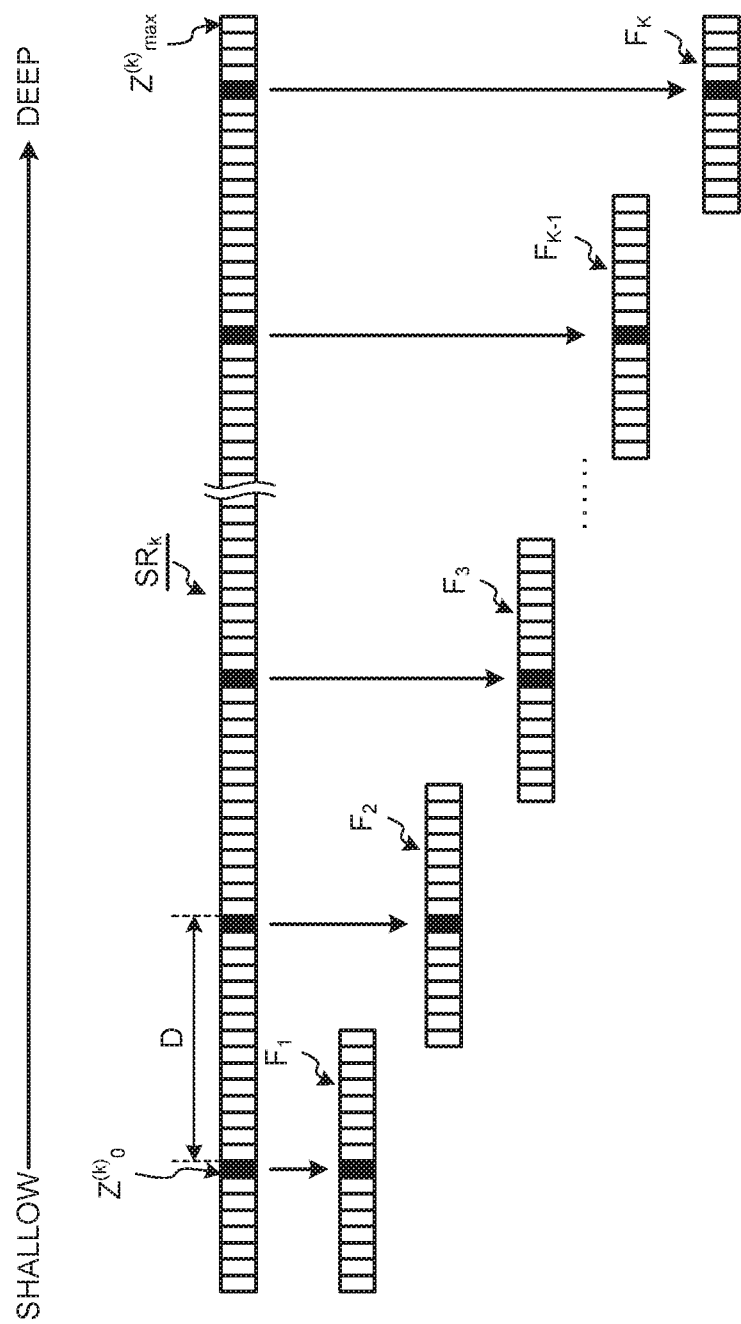
FIG. 4 is a schematic diagram illustrating a data array in one sound ray of an ultrasound signal.

FIG. 4 is a schematic diagram illustrating a data array on a single sound ray of an ultrasound signal. On a sound ray $SR_k$ illustrated in FIG. 4, each white or black rectangle represents data at one sampling point. On the sound ray $SR_k$, data located on the right side indicates sample data obtained from a deeper location relative to the ultrasound transducer 21 along the sound ray $SR_k$ (see arrow in FIG. 4). The sound ray $SR_k$ is discretized at time intervals corresponding to a sampling frequency (e.g., 50 MHz) in the A/D conversion performed by the transmitting and receiving unit 31. In FIG. 4, the eighth data position of the sound ray $SR_k$ having a number k is set as an initial value $Z^{(k)}_0$ in a direction of the reception depth z, but the position of the initial value can be arbitrarily set. A result of calculation performed by the frequency analysis unit 332 is obtained as a complex number, and the complex number is stored in the storage unit 37.

Data groups $F_j$ (j=1, 2, ... K) illustrated in FIG. 4 are the sample data groups to be subjected to the FFT processing. For performance of the FFT processing, generally, a sample data group needs to have the number of data elements of a power of 2. In this sense, the sample data groups $F_j$ (j=1, 2, ..., K−1) has the number of data elements of 16 (=$2^4$) as a normal data group, but a sample data group $F_K$ has the number of data elements of 12 as an abnormal data group. When the FFT processing is performed on the abnormal data group, zero data is inserted to cover the shortfall, thereby to generate a normal sample data group. This point will be described later in detail during an explanation of the processing of the frequency analysis unit 332 (see FIG. 9).

Figure 5:
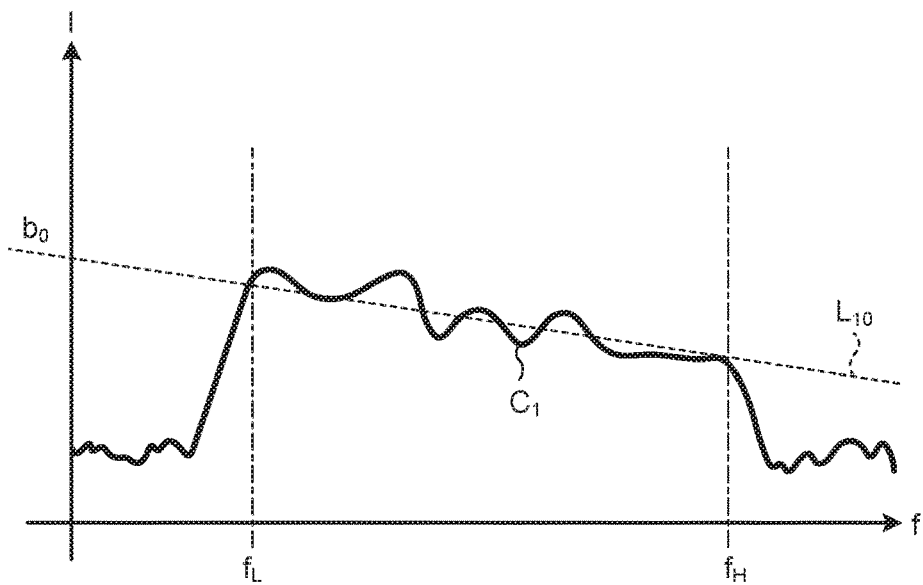
FIG. 5 is a graph illustrating an example of a frequency spectrum calculated by a frequency analysis unit of the ultrasound observation apparatus according to the first embodiment of the present invention.

FIG. 5 is a graph illustrating an example of the frequency spectrum calculated by the frequency analysis unit 332. The term "frequency spectrum" described here represents "frequency distribution of intensities at a reception depth z" obtained by performing the FFT processing on the sample data groups. Furthermore, the term "intensity" described here represents for example a parameter, such as voltage of echo signal, power of echo signal, acoustic pressure of ultrasound echo, or acoustic energy of ultrasound echo, or amplitude or a time integration value of a parameter, or combination thereof.

In FIG. 5, the horizontal axis represents frequency f. In addition, in FIG. 5, the vertical axis represents a common logarithm (decibel expression) $I=10 \log_{10}(I_0/I_c)$. The common logarithm has an amount obtained by dividing intensity $I_0$ by reference intensity $I_c$ (constant). In FIG. 5, the reception depth z is constant. A straight line $L_{10}$ illustrated in FIG. 5 will be described later. Note that, in the first embodiment, a curved line and a straight line each include a set of discrete points.

In the frequency spectrum $C_1$ illustrated in FIG. 5, a lower limit frequency $f_L$ and an upper limit frequency $f_H$ of a frequency range used for subsequent calculation are parameters determined based on the frequency range of the ultrasound transducer 21, a frequency range of the pulsed signal transmitted by the transmitting and receiving unit 31, or the like. Hereinafter, in FIG. 5, a frequency range determined by the lower limit frequency $f_L$ and the upper limit frequency $f_H$ is referred to as "frequency range F".

In general, if the observation target is living tissue, the frequency spectrum tends to differ depending on characteristics of living tissue over which an ultrasound wave is scanned. This is because the frequency spectrum correlates with the size and number density of a scatterer scattering the ultrasound wave, an acoustic impedance, or the like. The term "characteristics of living tissue" described here represents for example malignant tumor (cancer), benign tumor, endocrine tumor, mucinous tumor, normal tissue, cyst, vascular channel, or the like.

The optimal attenuation rate setting unit 333 includes an approximation unit 333a, an attenuation correction unit 333b, and a statistical processing unit 333c. The approximation unit 333a approximates the frequency spectrum with a straight line to calculate the uncorrected features of the frequency spectrum, the attenuation correction unit 333b performs the attenuation correction on the uncorrected features calculated by the approximation unit 333a based on a plurality of attenuation rate candidate values to calculate the corrected feature, and the statistical processing unit 333c calculates a statistical dispersion of the corrected features calculated for all frequency spectra by the attenuation correction unit 333b, to extract an optimal attenuation rate from among the attenuation rate candidate values based on the calculated statistical dispersion. The optimal attenuation rate setting unit 333 calculates the optimal attenuation rate for one or more regions of interest (ROI) set in an ultrasound scan area (observation target region). In the first embodiment, the regions of interest are set without intersecting one another.

The approximation unit 333a performs regression analysis on the frequency spectrum in a predetermined frequency range, approximates the frequency spectrum with a linear expression (regression line), and calculates uncorrected features featuring the approximated linear expression. For example, in the frequency spectrum $C_1$ illustrated in FIG. 5, the approximation unit 333a performs regression analysis in the frequency range F, and approximates the frequency spectrum $C_1$ with the linear expression to obtain the regression line $L_{10}$. In other words, the approximation unit 333a calculates a slope $a_0$ and an intercept $b_0$ of the regression line $L_{10}$, and mid-band fit $c_0=a_0f_M+b_0$ as a value on the regression line at a center frequency $f_M=(f_L+f_H)/2$ in the frequency range F, as the uncorrected features.

The slope $a_0$ of the three uncorrected features correlates with the size of the scatterer scattering the ultrasound wave, and is generally considered to have a smaller value as the size of the scatterer is increased. Furthermore, the intercept $b_0$ correlates with the size of the scatterer, a difference in acoustic impedance, the number density (concentration) of the scatterers, or the like. Specifically, the intercept $b_0$ has a larger value as the size of the scatterer is increased, has a larger value as the difference in acoustic impedance is increased, and has a larger value as the number density of the scatterer is increased. The mid-band fit $c_0$ is an indirect parameter derived from the slope $a_0$ and the intercept $b_0$, and intensifies a spectrum at the center of an effective frequency range. Therefore, the mid-band fit $c_0$ is considered to have some correlation with the luminance value of the B-mode image in addition to the size of the scatterer, the difference in acoustic impedance, and the number density of the scatterer. The optimal attenuation rate setting unit 333 may approximate the frequency spectrum by a quadratic expression or higher order polynomial using regression analysis.

Correction performed by the attenuation correction unit 333b will be described. Generally, an ultrasound attenuation amount A (f,z) represents attenuation generated during reciprocation of an ultrasound wave between reception depth 0 and reception depth z, and is defined as change in intensity before and after the reciprocation (difference in decibel expression). The attenuation amount A(f,z) is empirically known to be proportional to frequency in homogeneous tissue, and is expressed by the following formula (1).

$$A(f,z)=2\alpha z f \quad (1)$$

In this formula, a constant α of proportion is an amount called attenuation rate, and is an attenuation amount per unit length and unit frequency. Furthermore, z is a reception depth of an ultrasound wave, and f is a frequency. When the observation target is a living body, a specific value of the attenuation rate α is determined depending on a portion of the living body. A unit of the attenuation rate α is for example dB/cm/MHz. In the first embodiment, in order to set the attenuation rate (optimal attenuation rate) most suitable for the observation target, the attenuation correction unit 333b performs attenuation correction on the attenuation rate candidate values. The attenuation rate candidate values will be described in detail with reference to FIGS. 10 and 11.

The attenuation correction unit 333b performs attenuation correction on the uncorrected feature (slope $a_0$, intercept $b_0$, mid-band fit $c_0$) extracted by the approximation unit 333a according to the following formulas (2) to (4) to calculate the corrected features a, b, and c.

$$a=a_0+2\alpha z \quad (2)$$

$$b=b_0 \quad (3)$$

$$c=c_0+A(f_M,z)=c_0+2\alpha z f_M(=af_M+b) \quad (4)$$

As apparent from formulas (2) and (4), the attenuation correction unit 333b performs correction on a larger reception depth z of ultrasound wave with a larger correction amount. Furthermore, according to formula (3), correction relating to the intercept is identity transformation. This is because the intercept is a frequency component corresponding to frequency 0 (Hz), and is not influenced by the attenuation.

Figure 6:
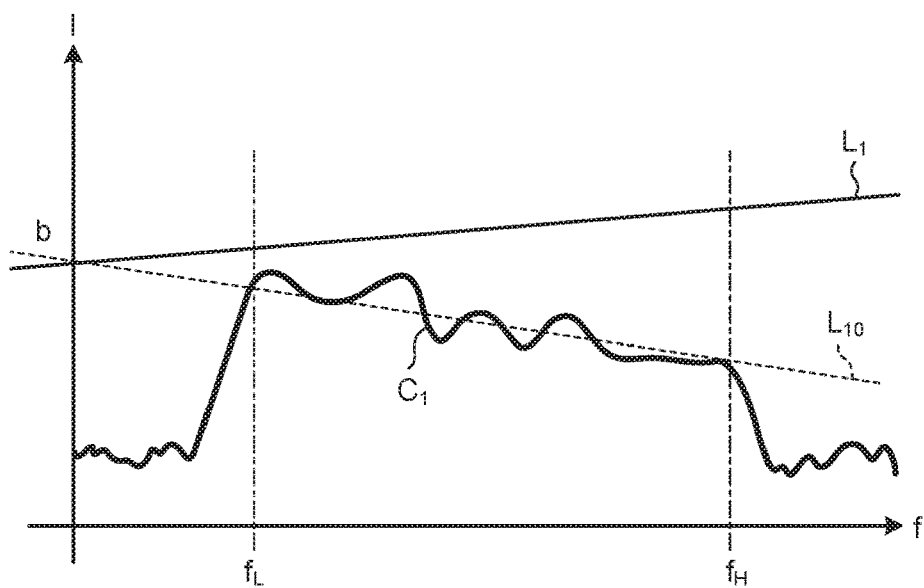
FIG. 6 is a graph illustrating a straight line having, as a parameter, a corrected feature corrected by an attenuation correction unit of the ultrasound observation apparatus according to the first embodiment of the present invention.

FIG. 6 is a graph illustrating a straight line having, as parameters, the corrected features a, b, and c corrected by the attenuation correction unit 333b. A straight line $L_1$ is expressed as the following formula:

$$I=af+b=(a_0+2\alpha z)f+b_0 \quad (5)$$

As is clear from formula (5), the straight line $L_1$ has a larger slope $(a>a_0)$ and the same intercept $(b=b_0)$, compared with the straight line $L_{10}$ before the attenuation correction.

The statistical processing unit 333c calculates variance as the statistical dispersion of the corrected features, for each region of interest. The corrected features are calculated for the attenuation rate candidate values by the attenuation correction unit 333b, for all frequency spectrums. Then, the statistical processing unit 333c extracts an attenuation rate candidate value at which the variance is minimum, as the optimal attenuation rate for each region of interest. Note that, when the attenuation correction is performed for a plurality of kinds of features, the statistical processing unit 333c only needs to calculate variance of one kind of corrected features appropriately set. If there is a plurality of attenuation rate candidate values at which the variance is minimum in the same region of interest, the statistical processing unit 333c preferably employs, as the optimal attenuation rate, an average value of the attenuation rate candidate values at which the variance is minimum, for example.

Two of the above-mentioned three corrected features a, b, and c are independent. In addition, the corrected feature b does not depend on the attenuation rate. Therefore, when the optimal attenuation rate is set for the corrected features a and c, the statistical processing unit 333c may calculate variance of one of the corrected features a and c. However, a corrected feature used to set the optimal attenuation rate by the optimal attenuation rate setting unit 333 is preferably a corrected feature used to generate an attenuation rate image data by an attenuation rate image data generation unit 342. That is, when the attenuation rate image data generation unit 342 uses the slope as a corrected feature to generate the attenuation rate image data, the variance of the corrected feature a is further preferably applied, and when the attenuation rate image data generation unit 342 uses the mid-band fit as a corrected feature to generate the attenuation rate image data, the variance of the corrected feature c is further preferably applied. This is because formula (1) for providing the attenuation amount A(f,z) is merely ideal formula, and the following formula (6) is an appropriate formula in fact.

$$A(f,z)=2\alpha z f+2\alpha_1 z \quad (6)$$

In formula (6), $\alpha_1$ of the second term on the right side is a coefficient representing a magnitude of change in signal intensity in proportion to the reception depth z of ultrasound wave, and corresponds to the attenuation rate per unit length. The coefficient $\alpha_1$ is a coefficient representing the change in signal intensity caused by inhomogeneous tissue to be observed, change of the number of channels upon beam synthesis, or the like. For the presence of the second term on the right side of formula (6), when the corrected feature c is used to set the optimal attenuation rate, the variance of the corrected feature c is preferably applied for accurate attenuation correction (see formula (4)). In contrast, when the corrected feature a is used to set the optimal attenuation rate, the variance of the corrected feature a is preferably applied for accurate attenuation correction, eliminating influence of the second term on the right side. The corrected feature a is a coefficient in proportion to the frequency f. Note that, when the unit of attenuation rate α is dB/cm/MHz, the unit of coefficient $\alpha_1$ is dB/cm.

Here, the reason why the optimal attenuation rate can be set based on the statistical dispersion will be described. When the optimal attenuation rate is applied to the observation target, it is considered that the features are converged to a value unique to the observation target, regardless of a distance between the observation target and the ultrasound transducer 21, and the statistical dispersion is reduced. In contrast, when an attenuation rate candidate value, unsuitable for the observation target, is employed as the optimal attenuation rate, it is considered that excessive or insufficient attenuation correction causes inconsistency in the feature according to the distance between the observation target and the ultrasound transducer 21, and statistical dispersion of the features is increased. Accordingly, an attenuation rate candidate value at which the statistical dispersion is minimum is the optimal attenuation rate for the observation target.

Figure 7:
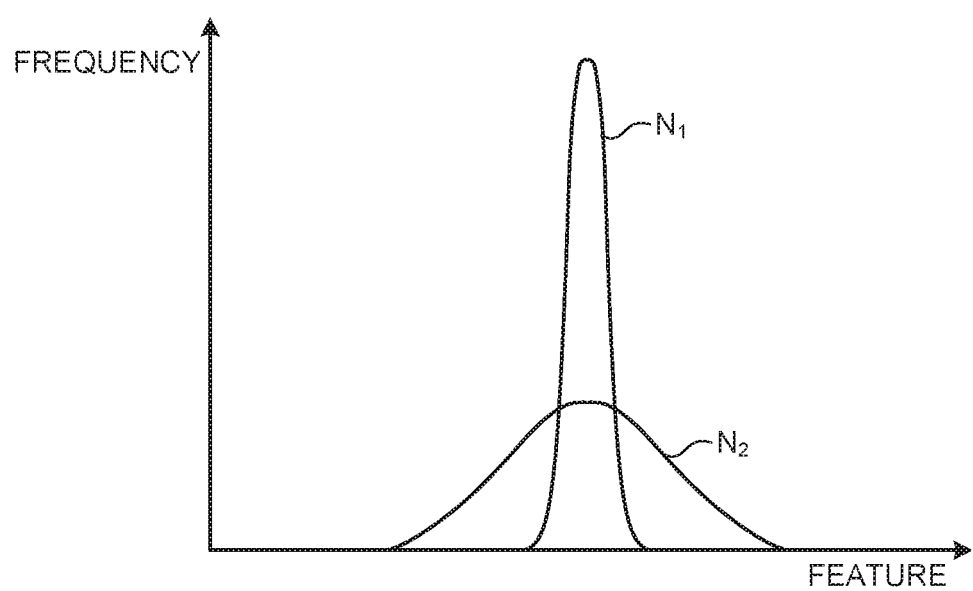
FIG. 7 is a graph schematically illustrating an exemplary distribution of corrected features each subjected to attenuation correction based on two different attenuation rate candidate values, for the same region of interest.

FIG. 7 is a graph schematically illustrating an exemplary distribution of corrected features each subjected to attenuation correction based on two different attenuation rate candidate values, for the same region of interest. In FIG. 7, the horizontal axis represents corrected feature and the vertical axis represents frequency. Two distribution curves $N_1$ and $N_2$ illustrated in FIG. 7 have the same sum of frequency. As illustrated in FIG. 7, the distribution curve $N_1$ has a small statistical dispersion of the features (small variance), compared with the distribution curve $N_2$, and results in a steep peak. Accordingly, when setting the optimal attenuation rate from two attenuation rate candidate values corresponding to these two distribution curves $N_1$ and $N_2$, the optimal attenuation rate setting unit 333 sets an attenuation rate candidate value corresponding to the distribution curve $N_1$, as the optimal attenuation rate.

The image processing unit 34 has a B-mode image data generation unit 341 for generating a B-mode image data as an ultrasound image displaying brightness obtained by converting the amplitude of the echo signal, and the attenuation rate image data generation unit 342 for generating the attenuation rate image data displaying information on the optimal attenuation rate set by the optimal attenuation rate setting unit 333.

The B-mode image data generation unit 341 performs signal processing using a known technique such as gain processing or contrast processing, on the B-mode reception data received from the signal processing unit 32, performs decimation of data or the like according to a data step width determined according to a display range of an image in the display device 4, and generates the B-mode image data. The B-mode image is a grayscale image having equal R (red), G (green), and B (blue) values, as variables, in an RGB color system employed as a color space.

The B-mode image data generation unit 341 performs coordinate conversion on the B-mode reception data output from the signal processing unit 32 to rearrange the B-mode reception data so that a scanned range may be spatially appropriately expressed, then, performs interpolation between B-mode reception data to fill voids in the B-mode reception data, and generates the B-mode image data. The B-mode image data generation unit 341 outputs the generated B-mode image data to the attenuation rate image data generation unit 342.

The attenuation rate image data generation unit 342 superimposes visual information corresponding to the optimal attenuation rate determined for each region of interest, on a corresponding region of interest in the B-mode image data, and generates the attenuation rate image data. The visual information is stored in a visual information storage unit 374 (described later) of the storage unit 37. In the first embodiment, one set of visual information is added for one region of interest.

The control unit 36 uses a central processing unit (CPU), various calculation circuits, or the like having a calculation and control functions. The control unit 36 reads information stored in the storage unit 37 from the storage unit 37, and executes various calculation processing relating to an operation method for the ultrasound observation apparatus 3 to collectively control the ultrasound observation apparatus 3. Note that, the control unit 36 can share a CPU or the like with the signal processing unit 32 and the calculation unit 33.

The storage unit 37 has a spectral information storage unit 371 for storing information on the frequency spectra calculated by the frequency analysis unit 332 with the reception depth and reception direction thereof, a region-of-interest information storage unit 372 for storing information on the regions of interest set in an observation target region, a feature information storage unit 373 for storing information on feature, for each region of interest, and the visual information storage unit 374 for storing the visual information added to an image according to a value of the optimal attenuation rate.

The regions of interest stored in the region-of-interest information storage unit 372 do not intersect one another. If a user may change settings of a region of interest through the input unit 35, the region-of-interest information storage unit 372 may only store the latest region-of-interest information in which the settings of the region of interest has changed most recently, or may store, together with the latest region-of-interest information, part or all of region-of-interest information in which the setting of the region of interest has changed in the past.

The feature information storage unit 373 stores the uncorrected feature calculated by the approximation unit 333a, in association with a reception depth and reception direction at a point where the uncorrected feature is calculated, and region-of-interest information to which the point belongs. Furthermore, the feature information storage unit 373 stores a plurality of corrected features calculated by the attenuation correction unit 333b and variance for the statistical dispersion of the corrected features, in association with the attenuation rate candidate values and the region of interest.

The visual information stored in the visual information storage unit 374 is for example any of luminance, hue, brightness, and saturation, and has a value determined according to a value of the attenuation rate. Note that, the visual information storage unit 374 may store a plurality of kinds of visual information in association with the attenuation rate. In this configuration, the user preferably selects desired visual information through the input unit 35.

Besides the above, the storage unit 37 stores, for example, information required for the amplification processing (relationship between the amplification factor and the reception depth illustrated in FIG. 2), information required for the amplification correction processing (relationship between the amplification factor and the reception depth illustrated in FIG. 3), information required for the attenuation correction processing (see formula (1)), information for a window function required for the frequency analysis processing (Hamming, Hanning, Blackman, et al.), and the like.

Furthermore, the storage unit 37 stores various programs including an operation program for executing the operation method for the ultrasound observation apparatus 3. The operation program can be recorded in a computer-readable recording medium such as a hard disk, a flash memory, a CD-ROM, a DVD-ROM, or a flexible disk, for wide distribution. Note that, the above-mentioned various programs can be obtained by being downloaded through a communication network. Here, the communication network includes for example an existing wired or wireless public switched telephone network, local area network (LAN), or wide area network (WAN).

The storage unit 37 having above-mentioned configuration uses a read only memory (ROM) in which various programs or the like are previously installed, a random access memory (RAM) storing calculation parameters, data, or the like for processing, or the like.

Figure 8:
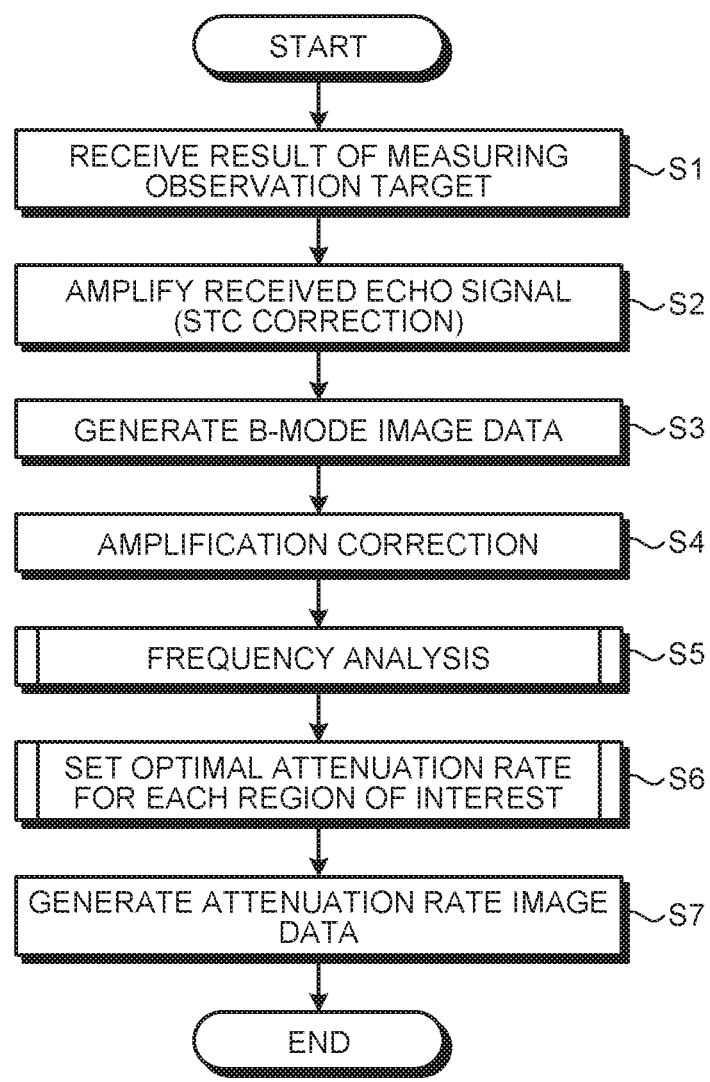
FIG. 8 is a flowchart illustrating an outline of a process performed by the ultrasound observation apparatus according to the first embodiment of the present invention.

FIG. 8 is a flowchart illustrating an outline of a process performed by the ultrasound observation apparatus 3 having a configuration described above. Specifically, FIG. 8 is a flowchart illustrating an outline of a process of reception of the echo signal from the ultrasound endoscope 2 by the ultrasound observation apparatus 3 and processes subsequent thereto. Processing performed by the ultrasound observation apparatus 3 will be described below with reference to FIG. 8. First, the ultrasound observation apparatus 3 receives, from the ultrasound endoscope 2, an echo signal as a result of measuring the observation target by the ultrasound transducer 21 (step S1).

The signal amplification unit 311 receiving the echo signal from the ultrasound transducer 21 performs amplification of the echo signal (step S2). Here, the signal amplification unit 311 for example performs the amplification (STC correction) of the echo signal based on the relationship between the amplification factor and the reception depth illustrated in FIG. 2.

Then, the B-mode image data generation unit 341 uses the echo signal amplified by the signal amplification unit 311 to generate output B-mode image data and output the B-mode image data to the display device 4 (step S3). The display device 4 receiving the B-mode image data displays a B-mode image corresponding to the B-mode image data.

The amplification correction unit 331 performs amplification correction on RF data output from the transmitting and receiving unit 31 to have a constant amplification factor regardless of the reception depth (step S4). Here, the amplification correction unit 331 performs the amplification correction for example to establish the relationship between the amplification factor and the reception depth illustrated in FIG. 3.

Figure 9:
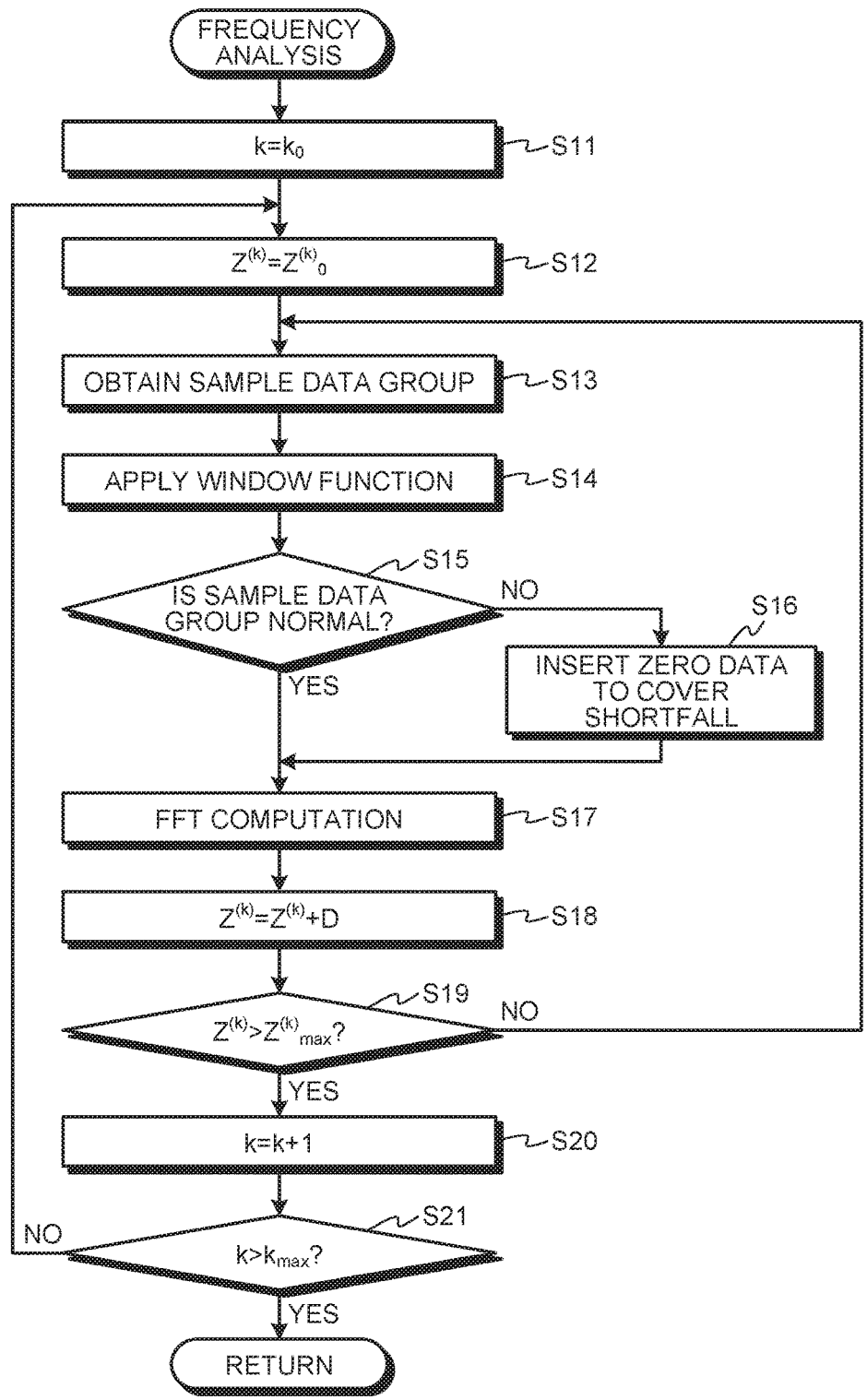
FIG. 9 is a flowchart illustrating an outline of a process performed by the frequency analysis unit of the ultrasound observation apparatus according to the first embodiment of the present invention.

Thereafter, the frequency analysis unit 332 performs frequency analysis using FFT on the RF data of each sound ray after performance of the amplification correction to calculate the frequency spectra for all the sample data groups (step S5). FIG. 9 is a flowchart illustrating an outline of a process performed by the frequency analysis unit 332 in step S5. The frequency analysis processing will be described in detail below with reference to the flowchart illustrated in FIG. 9.

First, the frequency analysis unit 332 sets a counter k for identifying a sound ray to be analyzed, to $k_0$ (step S11).

Next, the frequency analysis unit 332 sets the initial value $Z^{(k)}_0$ of a data position (corresponding to reception depth) $Z^{(k)}$ representative of a series of data groups (sample data groups) generated for FFT calculation (step S12). For example, FIG. 4 illustrates the eighth data position of the sound ray $SR_k$ set as the initial value $Z^{(k)}_0$, as described above.

Then, the frequency analysis unit 332 obtains the sample data groups (step S13), and applies the window function stored in the storage unit 37 to the obtained sample data groups (step S14). As described above, the window function is applied to the sample data groups to avoid the sample data groups being made discrete on a boundary, and to prevent artifact from being generated.

Next, the frequency analysis unit 332 determines whether the sample data group at the data position $Z^{(k)}$ is a normal data group (step S15). As described with reference to FIG. 4, the sample data group needs to have the number of data elements of a power of 2. Hereinafter, the number of data elements of the normal sample data group is defined as $2^n$ (n is a positive integer). In the embodiment, the data position $Z^{(k)}$ is set to be at the center of the sample data group to which $Z^{(k)}$ belongs, as much as possible. Specifically, the number of data elements of the normal sample data group is $2^n$, so that $Z^{(k)}$ is set at the $2^n/2$ ($=2^{n-1}$)-th position near the center of the sample data group. In this configuration, the normal sample data group represents that the sample data group has $2^{n-1}-1$ (=N) data elements previous to the data position $Z^{(k)}$, and $2^{n-1}$ (=M) data elements subsequent to the data position $Z^{(k)}$. As illustrated in FIG. 4, the sample data groups $F_j$ (j=1, 2, . . . , K−1) are normal. Note that, in FIG. 4, an example of n=4 (N=7, M=8) is illustrated.

As a result of determination in step S15, when the sample data group at the data position $Z^{(k)}$ is normal (step S15: Yes), the frequency analysis unit 332 proceeds to step S17 described later.

As a result of determination in step S15, when the sample data group at the data position $Z^{(k)}$ is not normal (step S15: No), the frequency analysis unit 332 inserts zero data to cover the shortfall to generate the normal sample data group (step S16). To the sample data group (for example, the sample data group $F_K$ in FIG. 4) determined not to be normal in step S15, the window function is applied, before addition of the zero data. Therefore, even if the zero data is inserted into the sample data group, discrete data is not generated. After step S16, the frequency analysis unit 332 proceeds to step S17 described later.

In step S17, the frequency analysis unit 332 perform FFT computation using the sample data groups, and obtain the frequency spectra as an amplitude frequency distribution (step S17). The frequency spectrum $C_1$ illustrated in FIG. 5 is an example of frequency spectrum obtained as a result of step S17.

Next, the frequency analysis unit 332 changes the data position $Z^{(k)}$ to have a step width D (step S18). The step width D is previously stored in the storage unit 37. In FIG. 4, an example of D=15 is illustrated. The step width D preferably coincides with the data step width used for generation of the B-mode image data by the B-mode image data generation unit 341, but when a calculation amount in the frequency analysis unit 332 is desired to be reduced, a value larger than the data step width may be set as the step width D.

Then, the frequency analysis unit 332 determines whether the data position $Z^{(k)}$ is larger than a maximum value $Z^{(k)}_{max}$ in the sound ray $SR_k$ (step S19). When the data position $Z^{(k)}$ is larger than the maximum value $Z^{(k)}_{max}$ (step S19: Yes), the frequency analysis unit 332 increments the counter k by 1 (step S20). This means that the processing is shifted to a next sound ray. In contrast, when the data position $Z^{(k)}$ is not larger than the maximum value $Z^{(k)}_{max}$ (step S19: No), the frequency analysis unit 332 returns to step S13.

After step S20, the frequency analysis unit 332 determines whether the counter k has a value larger than the maximum value $k_{max}$ (step S21). When the counter k has a value larger than the maximum value $k_{max}$ (step S21: Yes), the frequency analysis unit 332 finishes a series of frequency analysis processing. In contrast, when the counter k has a value not larger than the maximum value $k_{max}$ (step S21: No), the frequency analysis unit 332 returns to step S12. The maximum value $k_{max}$ is an arbitrary value input for instruction through the input unit 35 by the user such as an operator, or a value previously set in the storage unit 37.

As described above, the frequency analysis unit 332 performs a plurality of FFT calculations for each of ($k_{max}-k_0+1$) sound rays in an analysis target region. Results of the FFT calculations are stored in the spectral information storage unit 371 together with the reception depths and the reception directions.

Note that, in the above explanation, the frequency analysis unit 332 performs the frequency analysis processing for all areas receiving the ultrasound signal, but the input unit 35 may be configured to receive input of settings of a partial region which is divided into a specific depth width and sound ray width, and perform frequency analysis processing only in the set partial region.

Figure 10:
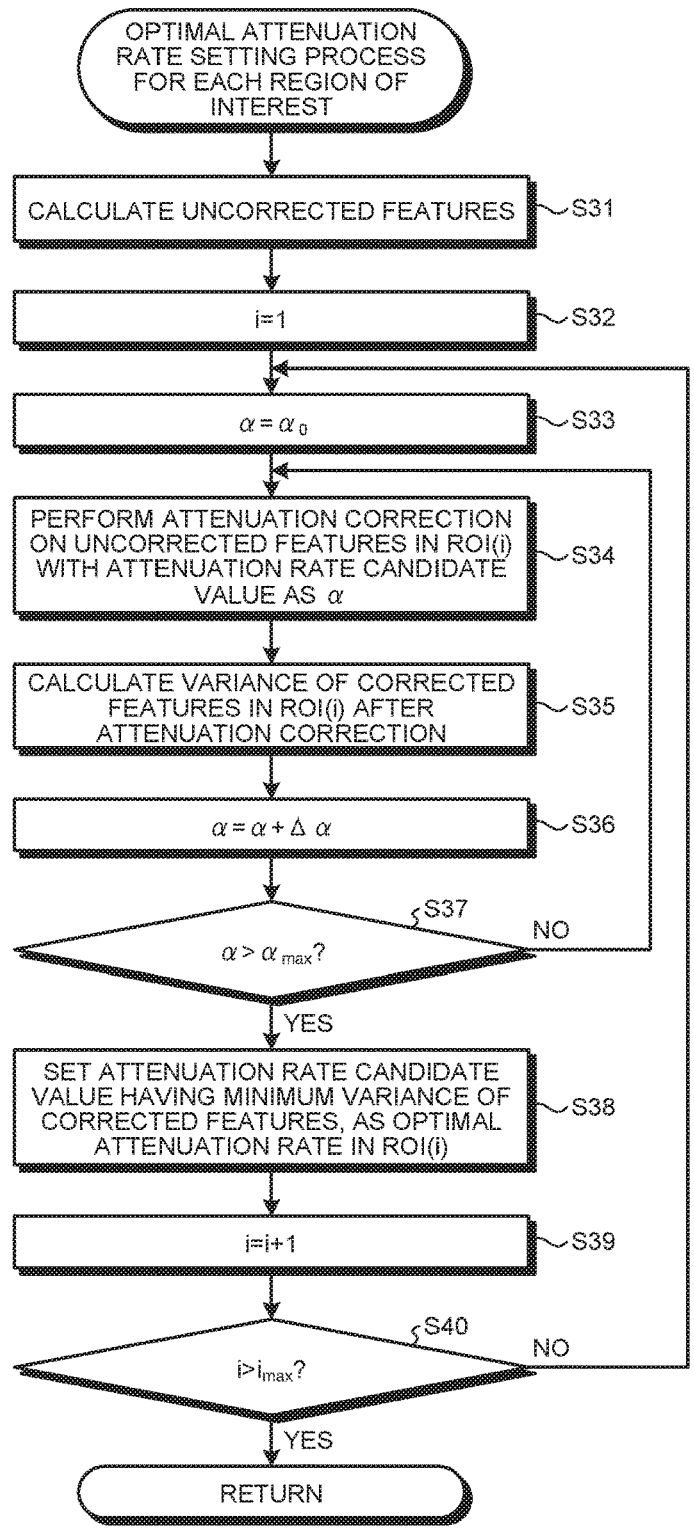
FIG. 10 is a flowchart illustrating an outline of an optimal attenuation rate setting process for each region of interest, performed by the ultrasound observation apparatus according to the first embodiment of the present invention.

Following the above-described frequency analysis processing in step S5, the optimal attenuation rate setting unit 333 sets an optimal attenuation rate for each region of interest (step S6). FIG. 10 is a flowchart illustrating an outline of a process in step S6. The processing in step S6 will be described in detail below with reference to FIG. 10.

First, the approximation unit 333a performs regression analysis on the frequency spectra calculated by the frequency analysis unit 332 to calculate uncorrected features corresponding to the frequency spectra (step S31). Specifically, the approximation unit 333a performs regression analysis on the frequency spectra for approximate with a linear expression to calculate the slope $a_0$, the intercept $b_0$, and the mid-band fit $c_0$ as the uncorrected features. For example, the straight line $L_{10}$ illustrated in FIG. 5 is a regression line which is obtained by approximation of the frequency spectrum $C_1$ in the frequency range F by the approximation unit 333a, using regression analysis. The uncorrected feature is stored in the feature information storage unit 373, together with the reception depth and the reception direction at the point where the uncorrected feature is calculated, and the region-of-interest information to which the calculated point belongs.

Then, the optimal attenuation rate setting unit 333 sets a counter i for identifying a region of interest to an initial value 1 (step S32).

Then, the optimal attenuation rate setting unit 333 sets a value of an attenuation rate candidate value α, applied upon attenuation correction described later, to a predetermined initial value $α_0$ (step S33). The value of the initial value $α_0$ is preferably stored by the storage unit 37 previously so that the optimal attenuation rate setting unit 333 may refer to the storage unit 37.

Next, the attenuation correction unit 333b performs attenuation correction on an uncorrected feature corresponding to each frequency spectrum in a region of interest ROI(i), with the attenuation rate candidate value as α, to calculate a corrected feature, and stores the corrected feature in the feature information storage unit 373, in association with the attenuation rate candidate value α and information of the region of interest ROI(i) (step S34). The straight line $L_1$ illustrated in FIG. 6 is an example of a straight line obtained by the attenuation correction processing performed by the attenuation correction unit 333b.

In step S34, the attenuation correction unit 333b calculates the corrected features by substituting a data position $Z=(f_{sp}/2v_s) Dn$ obtained by using a data array of a sound ray of a ultrasound signal, into the reception depth z in the above-mentioned formulas (2) and (4). Here, $f_{sp}$ is sampling frequency of data, $v_s$ is a sound velocity, D is a data step width, n is the number of data steps from the first data of a sound ray to a data position of a sample data group to be processed. For example, when the sampling frequency of data $f_{sp}$ is 50 MHz, the sound velocity $v_s$ is 1530 m/sec, and the step width D is 15 employing the data array illustrated in FIG. 4, z=0.2295 n (mm) is obtained.

Thereafter, the statistical processing unit 333c calculates variance of the corrected features obtained by attenuation correction performed on the frequency spectra by the attenuation correction unit 333b, and stores the variance in the feature information storage unit 373, in association with the attenuation rate candidate values α and the information of the region of interest ROI(i) (step S35). When the corrected features include the slope a and the mid-band fit c, the statistical processing unit 333c calculates variance of one of the corrected features a and c, as described above. In step S35, when the attenuation rate image data generation unit 342 uses the slope to generate attenuation rate image data, the variance of the corrected feature a is preferably applied, and when the attenuation rate image data generation unit 342 uses the mid-band fit to generate attenuation rate image data, the variance of the corrected feature c is preferably applied.

Next, the optimal attenuation rate setting unit 333 increases the value of the attenuation rate candidate value α by Δα (step S36), and compares the increased attenuation rate candidate value α with a predetermined maximum value $α_{max}$ (step S37). As a result of the comparison in step S37, when the attenuation rate candidate value α is larger than the maximum value $α_{max}$ (step S37: Yes), processing of the optimal attenuation rate setting unit 333 proceeds to step S38. In contrast, as a result of the comparison in step S37, when the attenuation rate candidate value α is not larger than the maximum value $α_{max}$ (step S37: No), processing of the optimal attenuation rate setting unit 333 returns to step S34.

In step S38, the statistical processing unit 333c refers to variance for each attenuation rate candidate value in the region of interest ROI(i) stored in the feature information storage unit 373 to extract an attenuation rate candidate value at which the variance is minimum, and sets this attenuation rate candidate value as the optimal attenuation rate of the region of interest ROI(i) (step S38).

Figure 11:
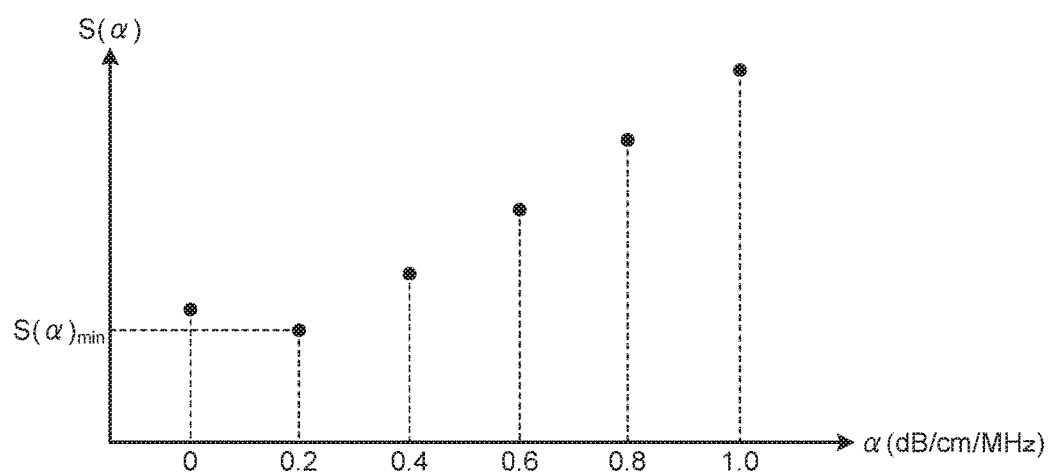
FIG. 11 is a graph illustrating an outline of processing performed by an optimal attenuation rate setting unit of the ultrasound observation apparatus according to the first embodiment of the present invention.

FIG. 11 is a graph illustrating an outline of processing performed by the statistical processing unit 333c. Specifically, FIG. 11 is a graph illustrating an example of a relationship between the attenuation rate candidate value α and variance S(α), where $α_0$=0 (dB/cm/MHz), $α_{max}$=1.0 (dB/cm/MHz), and Δα=0.2 (dB/cm/MHz). As illustrated in FIG. 11, when the attenuation rate candidate value α is 0.2 (dB/cm/MHz), the variance takes a minimum value $S(α)_{min}$. Accordingly, as illustrated in FIG. 11, the statistical processing unit 333c sets α=0.2 (dB/cm/MHz) as the optimal attenuation rate.

Thereafter, the optimal attenuation rate setting unit 333 increments the counter i by 1 (step S39), and compares the counter i with a predetermined maximum value $i_{max}$ (step S40). As a result of the comparison in step S40, when the counter i is larger than the maximum value $i_{max}$ (step S40: Yes), the optimal attenuation rate setting unit 333 finishes a series of processing. In contrast, as a result of the comparison in step S40, when the counter i is not larger than the maximum value $i_{max}$ (step S40: No), processing of the optimal attenuation rate setting unit 333 returns to step S33.

Returns to the flowchart of FIG. 8, the processing in step S7 will be described. The attenuation rate image data generation unit 342 refers to the visual information storage unit 374, and adds visual information corresponding to the optimal attenuation rate of each region of interest to pixels constituting each region of interest in the B-mode image data to generate the attenuation rate image data, and outputs the attenuation rate image data to the display device 4 (step S7). The display device 4 receives the attenuation rate image data, and displays an attenuation rate image corresponding to the attenuation rate image data.

After step S7, the ultrasound observation apparatus 3 finishes a series of processing. Note that processing of the ultrasound observation apparatus 3 is periodically repeated between steps S1 to S7.

Figure 12:
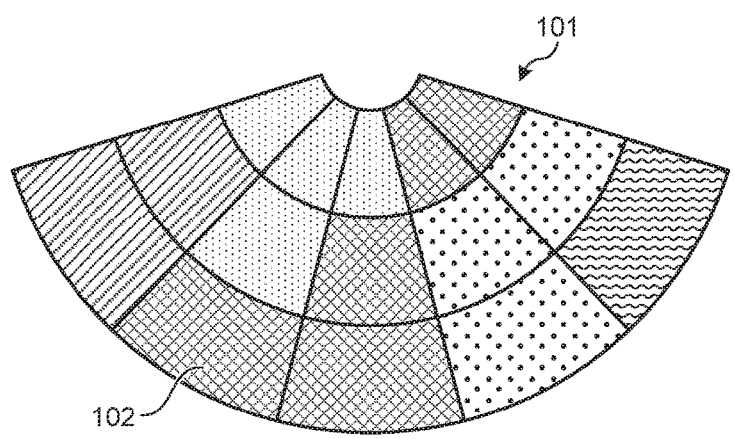
FIG. 12 is a schematic diagram illustrating an example of an attenuation rate image displayed on a display device in the first embodiment of the present invention.

FIG. 12 is a diagram illustrating an example of the attenuation rate image displayed on the display device 4. In an attenuation rate image 101 illustrated in FIG. 12, different sets of visual information are added to the regions of interest 102, respectively. Note that, FIG. 12 schematically illustrates the sets of visual information with patterns. Furthermore, in FIG. 12, specific display of the B-mode image is omitted for convenience. In the attenuation rate image 101 illustrated in FIG. 12, an example of a sector scan area of the ultrasound transducer 21 is illustrated. The sector scan area corresponds to the ultrasound transducer 21 being a convex transducer. In the attenuation rate image 101, 15 regions of interest 102 are set without intersecting one another. Specifically, the attenuation rate image 101 are divided into three parts along a radial direction (depth direction) of a sector, and further divided into five parts along a circumferential direction (scan direction) of the sector. The radial direction and the circumferential direction are divided at equal intervals, respectively. Note that, when the ultrasound transducer 21 is a linear transducer, the transducer has a rectangular (oblong, square) scan area, and when the ultrasound transducer 21 is a radial transducer, the transducer has a sector or annular scan area.

According to the first embodiment of the present invention having been described above, the optimal attenuation rates are set for the observation target, and the attenuation rate image data for displaying the information on the optimal attenuation rates is generated, and image data can be provided including information on the attenuation rates set according to the observation target. Thus, even if tissue to be observed has an inhomogeneous structure, the characteristics of the tissue can be accurately estimated based on ultrasound attenuation characteristics suitable for the observation target.

Furthermore, according to the first embodiment, for the regions of interest each partially constituting the observation target region, the optimal attenuation rates are calculated, visual information is added to each region of interest according to the optimal attenuation rate in each region of interest to generate the attenuation rate image data, so that even if tissue has an inhomogeneous structure, an image accurately displaying the attenuation characteristics according to the structure can be obtained. Accordingly, the user such as a physician can further accurately diagnose the characteristics of tissue while looking at the attenuation rate image.

First Modification of First Embodiment

Figure 13:
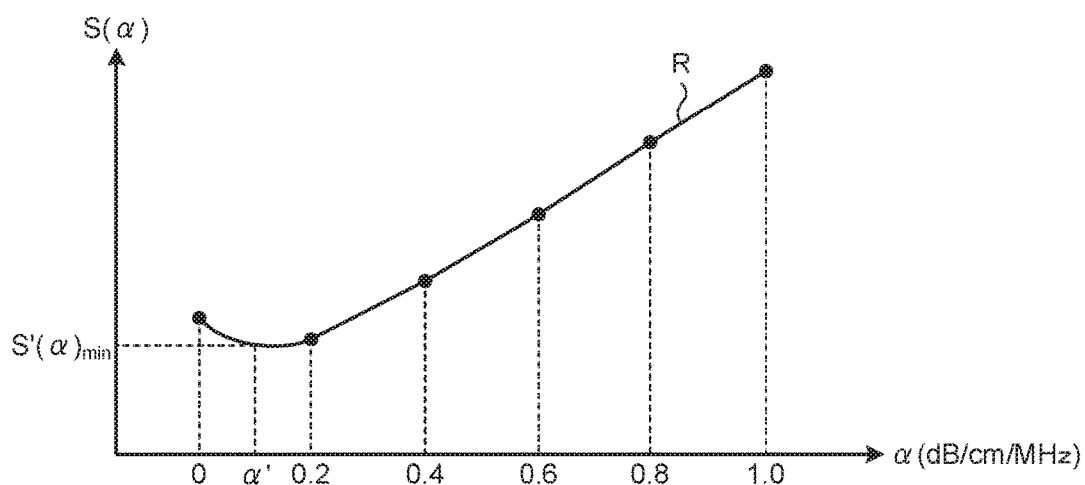
FIG. 13 is a graph illustrating an outline of processing performed by an optimal attenuation rate setting unit of an ultrasound observation apparatus according to a first modification of the first embodiment of the present invention.

FIG. 13 is a graph illustrating an outline of processing performed by the optimal attenuation rate setting unit of an ultrasound observation apparatus according to a first modification of the first embodiment. In the first modification, the optimal attenuation rate setting unit 333 obtains the variance as a function of attenuation rate candidate value, and sets a minimum value of the function as the optimal attenuation rate.

A curved line R illustrated in FIG. 13 is a curved line obtained by interpolating values of the variance $S(\alpha)$ in the attenuation rate candidate values $\alpha$, by the regression analysis performed by the approximation unit 333a before extraction of the optimal attenuation rates by the statistical processing unit 333c. Note that, in the first modification, values of variance $S(\alpha)$ in the attenuation rate candidate values $\alpha=0, 0.2, 0.4, 0.6, 0.8, 1.0$ (all dB/cm/MHz) are the same as those of FIG. 11. The statistical processing unit 333c uses this curved line R to calculate a minimum value $S'(\alpha)_{min}$ in $0$ (dB/cm/MHz)$\leq\alpha\leq 1.0$ (dB/cm/MHz), and extracts an attenuation rate candidate value $\alpha'$ corresponding to the minimum value $S'(\alpha)_{min}$ as the optimal attenuation rate. As illustrated in FIG. 13, the optimal attenuation rate $\alpha'$ has a value between 0 (dB/cm/MHz) and 0.2 (dB/cm/MHz).

According to the first modification, since the statistical processing unit 333c calculates the variance as the function of the attenuation rate candidate value, the optimal attenuation rate can be further accurately set.

Second Modification of First Embodiment

Figure 14:
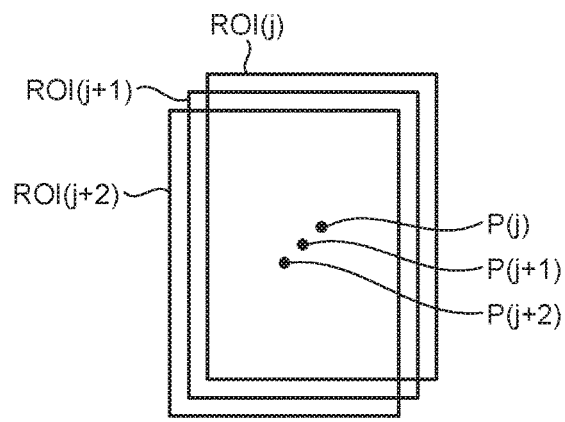
FIG. 14 is a schematic diagram illustrating an outline of a method for setting an optimal attenuation rate for each region of interest, performed by an ultrasound observation apparatus according to a second modification of the first embodiment of the present invention.

FIG. 14 is a schematic diagram illustrating an outline of a method for setting an optimal attenuation rate for each region of interest, performed by an ultrasound observation apparatus according to a second modification of the first embodiment. In the second modification, the regions of interest are set to intersect another region of interest including a nearest region of interest. Therefore, the ultrasound observation apparatus 3 adds visual information according to optimal attenuation rates of the regions of interest, to pixels at the centers of the regions of interest, while moving each region of interest on a pixel-by-pixel basis. For example, as illustrated in FIG. 14, the optimal attenuation rate setting unit 333 calculates an optimal attenuation rate for a region of interest ROI(j), and then adds visual information according to this optimal attenuation rate to a pixel P(j) at the center of the region of interest ROI(j). Similarly, the optimal attenuation rate setting unit 333 calculates optimal attenuation rates for regions of interest ROI(j+1) and ROI(j+2), and then adds visual information according to calculation results to a pixel P(j+1) at the center of the region of interest ROI(j+1), and a pixel P(j+2) at the center of the region of interest ROI(j+2).

Note that, in the second modification, instead of moving the region of interest on a pixel-by-pixel basis, the region of interest may be moved every several pixels within a range in which the regions of interest overlap one another before and after the movement. In this configuration, a pixel having the visual information is decimated. Therefore, for a pixel having no visual information, added based on the optimal attenuation rate, visual information is preferably added which is the same as that of a nearest one of the pixels having the visual information. When there is a plurality of nearest pixels, a statistical value (any of average value, mode value, median value, and maximum value) of visual information respectively added to a plurality of pixels is preferably added.

Furthermore, in the second modification, the pixel to which the visual information is added may be set at an arbitrary position in the region of interest other than the center thereof.

According to the second modification, the regions of interest overlap one another, and each of the regions of interest internally has a pixel at a predetermined position to which the visual information is added. Therefore, the attenuation rate image having further detailed information on attenuation rate can be provided.

Second Embodiment

Figure 15:
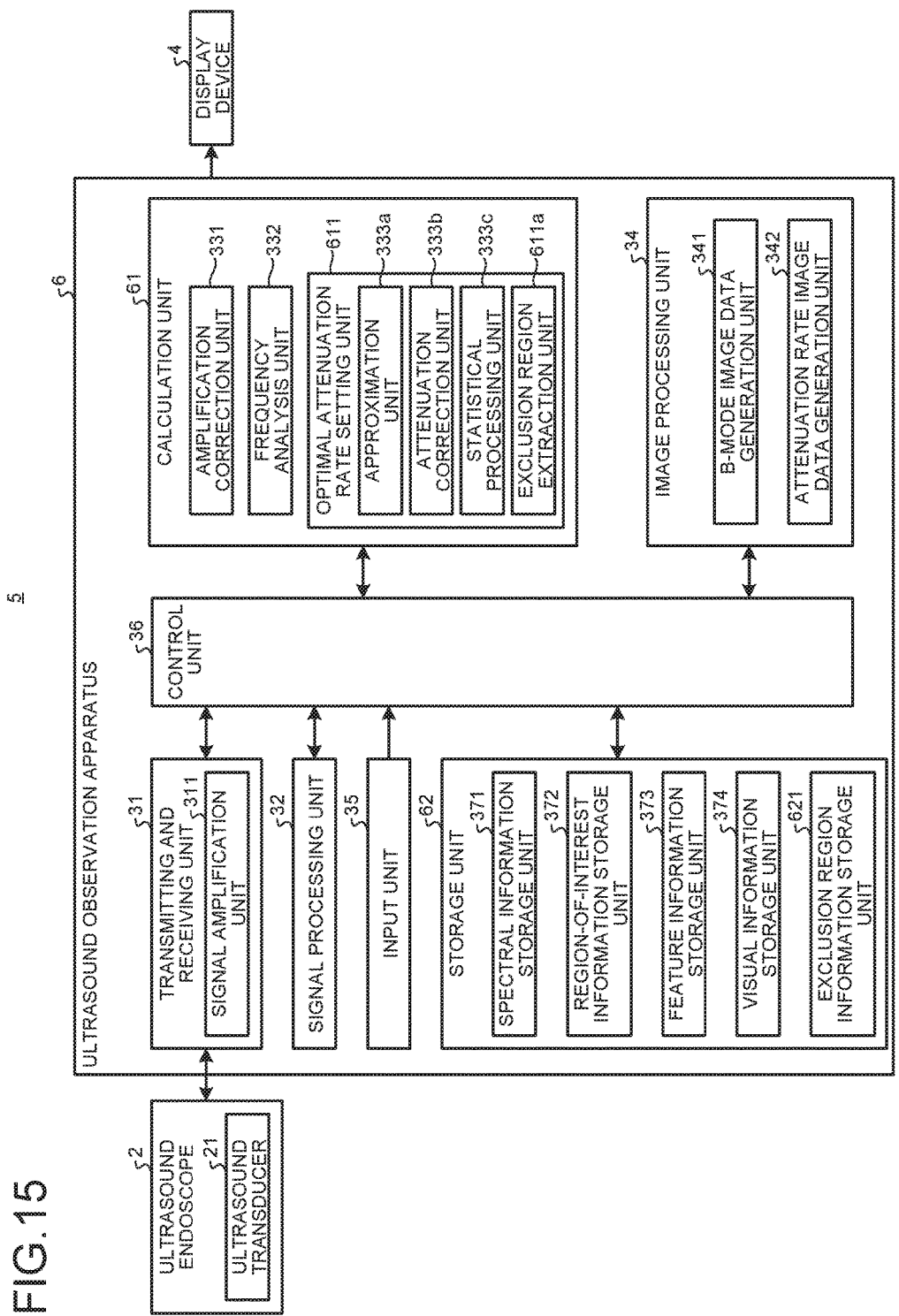
FIG. 15 is a block diagram illustrating a functional configuration of an ultrasound diagnostic system including an ultrasound observation apparatus according to a second embodiment of the present invention.

FIG. 15 is a block diagram illustrating a functional configuration of an ultrasound diagnostic system including an ultrasound observation apparatus according to a second embodiment of the present invention. The ultrasound diagnostic system 5 illustrated in FIG. 15 includes the ultrasound endoscope 2, an ultrasound observation apparatus 6, and the display device 4. The ultrasound endoscope 2 transmits an ultrasound wave to a subject, and receives an ultrasound wave reflected from the subject, the ultrasound observation apparatus 6 generates an ultrasound image based on an ultrasound signal acquired by the ultrasound endoscope 2, and the display device 4 displays the ultrasound image generated by the ultrasound observation apparatus 6.

The ultrasound observation apparatus 6 is different from the above-mentioned ultrasound observation apparatus 3, in configurations of a calculation unit 61 and a storage unit 62. The configurations of the calculation unit 61 and the storage unit 62 will be described below.

The calculation unit 61 includes the amplification correction unit 331, the frequency analysis unit 332, and an optimal attenuation rate setting unit 611. The optimal attenuation rate setting unit 611 includes an exclusion region extraction unit 611a for extracting, as an exclusion region, a set of points where values of the corrected features calculated in a region of interest fall within a predetermined range, in addition to the approximation unit 333a, the attenuation correction unit 333b, and the statistical processing unit 333c.

The exclusion region extracted by the exclusion region extraction unit 611a is for example a portion having a characteristic greatly different from a characteristic of tissue desired to be particularly diagnosed, in value of feature. For example, when using the mid-band fit as a feature, the value of the feature largely differs between malignant tumor, and a blood vessel and a blood vessel wall. Therefore, when the ultrasound observation apparatus 6 uses mid-band fit as the feature, a corrected feature value range may be set so that the blood vessel and the blood vessel wall are included in the exclusion region, and an attenuation rate image data suitable for observation of the malignant tumor can be generated.

The statistical processing unit 333c averages corrected features in a non-exclusion region in a corresponding region of interest, as the corrected features at the points in the exclusion region extracted by the exclusion region extraction unit 611a, and calculates variance of the corrected features in the region of interest. Note that, the statistical processing unit 333c may set, as the corrected feature, a statistical value such as a mode value, a median value, or a maximum value of the corrected features in the non-exclusion region, for the exclusion region of the region of interest.

The storage unit 62 has an exclusion region information storage unit 621 for storing a corrected feature value range to be excluded, in addition to the spectral information storage unit 371, the region-of-interest information storage unit 372, the feature information storage unit 373, and the visual information storage unit 374.

Figure 16:
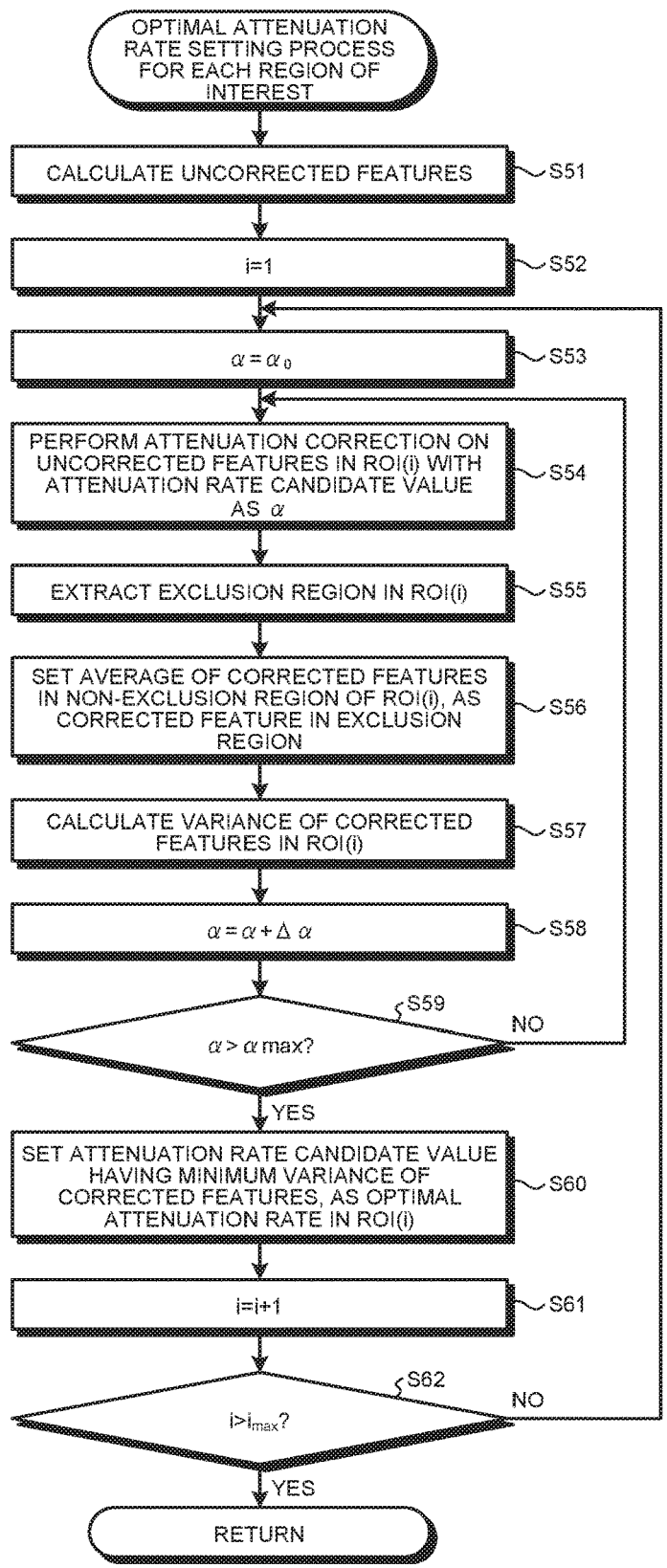
FIG. 16 is a flowchart illustrating an outline of an optimal attenuation rate setting process for each region of interest, which is performed by the ultrasound observation apparatus according to the second embodiment of the present invention.

FIG. 16 is a flowchart illustrating an outline of an optimal attenuation rate setting process for each region of interest, which is performed by the ultrasound observation apparatus 6. Steps S51 to S54 are sequentially correspond to steps S31 to S34 of FIG. 10.

Figure 17:
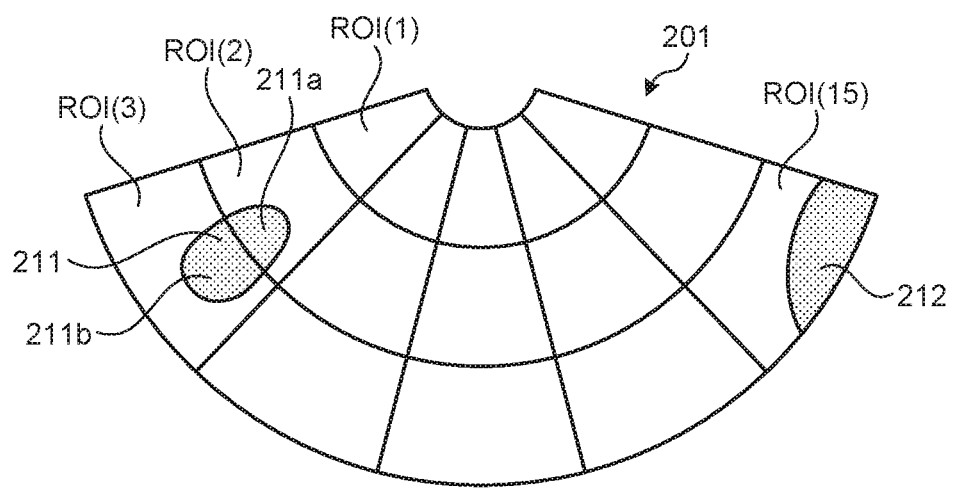
FIG. 17 is a schematic diagram illustrating an exclusion region extracted by an exclusion region extraction unit of the ultrasound observation apparatus according to the second embodiment of the present invention.

In step S55, the exclusion region extraction unit 611a refers to the exclusion region information storage unit 621 to extract an exclusion region in the region of interest ROI(i) (step S55). FIG. 17 is a schematic diagram illustrating the exclusion region in the ultrasound scan area, which is extracted by the exclusion region extraction unit 611a. In a scan area 201 illustrated in FIG. 17, two exclusion regions 211 and 212 are extracted. The exclusion region 211 is an area extending over two regions of interest ROI(2) and ROI(3), and the exclusion region 212 is an area in a region of interest ROI(15).

Then, the statistical processing unit 333c calculates the average of the corrected features in an area (non-exclusion region) in the region of interest ROI(i), not included in the exclusion region extracted by the exclusion region extraction unit 611a, and sets this average as a corrected feature at each point in the exclusion region (step S56). For example, as illustrated in FIG. 17, in the region of interest ROI(2), the average of the corrected features in the non-exclusion region is added to pixels constituting a partial region 211a included in the region of interest ROI(2) of the exclusion region 211. Similarly, in the region of interest ROI(3), the average of the corrected features in the non-exclusion region is added to pixels constituting a partial region 211b included in the region of interest ROI(3) of the exclusion region 211.

Next, the statistical processing unit 333c calculates variance of the corrected features at points in the region of interest ROI(i), and stores the variance in the feature information storage unit 373, in association with attenuation rates candidate values α (step S57). At this time, the statistical processing unit 333c calculates variance in the region of interest ROI(i), after a corrected feature in the exclusion region is set as the above-mentioned average.

Steps S58 to S62 are sequentially correspond to steps S36 to S40 of FIG. 10. Processing of the ultrasound observation apparatus 6, excluding the above-mentioned optimal attenuation rate setting process for each region of interest, is similar to the processing of the ultrasound observation apparatus 3 having been described above.

According to the second embodiment of the present invention having been described above, similarly to the first embodiment, even if tissue to be observed has an inhomogeneous structure, the characteristics of the tissue can be accurately estimated based on ultrasound attenuation characteristics suitable for the tissue to be observed. Furthermore, even if tissue has an inhomogeneous structure, an image accurately displaying attenuation characteristics according to the structure can be obtained.

Furthermore, according to the second embodiment, since the exclusion target region is extracted, and the statistical value of the corrected features of the non-exclusion region in the corresponding region of interest is added to the extracted exclusion target region, the optimal attenuation rate can be further accurately calculated based on the characteristics of tissue to be diagnosed.

Note that, in the second embodiment, the exclusion region extraction unit 611a may extract an exclusion region based on a luminance value of the B-mode image data. In this configuration, the exclusion region information storage unit 621 preferably stores a range of luminance values as the exclusion region.

Modification of Second Embodiment

Figure 18:
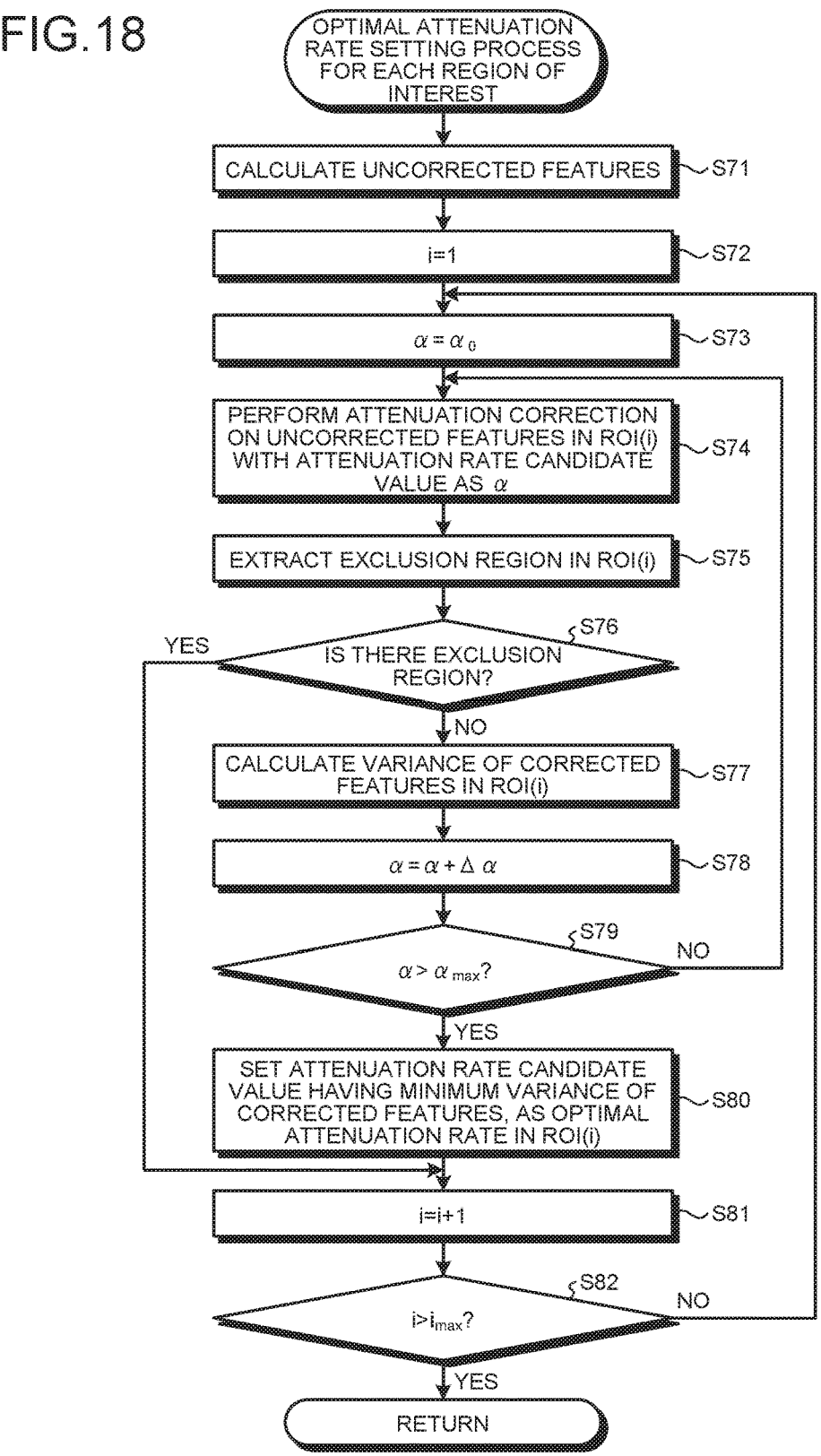
FIG. 18 is a flowchart illustrating an outline of an optimal attenuation rate setting process for each region of interest, performed by an ultrasound observation apparatus according to a modification of the second embodiment of the present invention.

FIG. 18 is a flowchart illustrating an outline of an optimal attenuation rate setting process for each region of interest, performed by an ultrasound observation apparatus 6 according to a modification of the second embodiment of the present invention. In the modification, the optimal attenuation rate setting unit 611 adds the visual information only to a region of interest not including the exclusion region extracted by the exclusion region extraction unit 611a. Steps S71 to S75 of FIG. 18 are sequentially correspond to steps S51 to S55 of FIG. 16.

As a result of exclusion region extraction processing in step S75, when the exclusion region is not extracted (step S76: No), processing of the optimal attenuation rate setting unit 611 proceeds to step S77. In contrast, as a result of the exclusion region extraction processing in step S75, when the exclusion region is extracted (step S76: Yes), processing of the optimal attenuation rate setting unit 611 proceeds to step S81.

In step S77, the statistical processing unit 333c calculates variance of the corrected features at points in the region of interest ROI(i), and stores the variance in the feature information storage unit 373 in association with the attenuation rate candidate values α (step S77). In the modification, this processing is performed only on the region of interest ROI(i) not having the exclusion region. Accordingly, as in the second embodiment described above, another value does not need to be added to the corrected feature of the exclusion region.

Steps S78 to S82 are sequentially correspond to steps S58 to S62 of FIG. 16.

Figure 19:
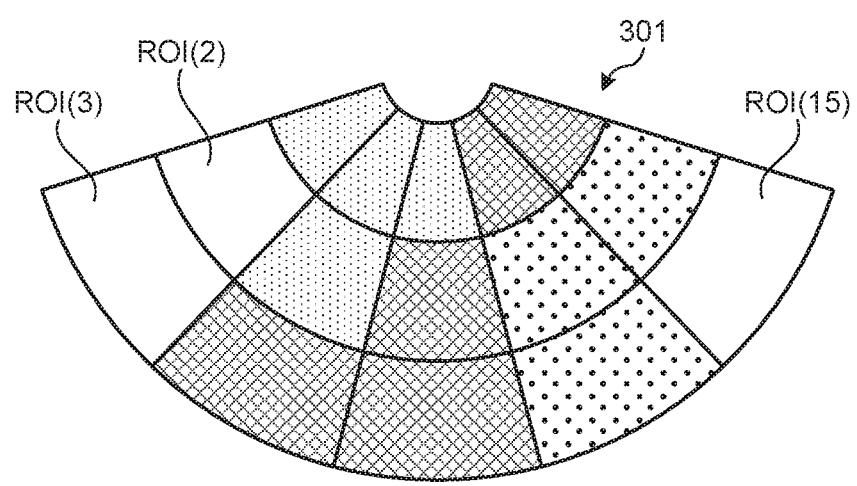
FIG. 19 is a schematic diagram illustrating an example of an attenuation rate image displayed on a display device in the modification of the second embodiment of the present invention.

FIG. 19 is a diagram illustrating an example of an attenuation rate image displayed on the display device 4 in the modification. An attenuation rate image 301 illustrated in FIG. 19 is generated when the exclusion regions 211 and 212 are extracted as illustrated in FIG. 17, and displayed on the display device 4. In the attenuation rate image 301, the visual information is not added to the regions of interest ROI(2) and ROI(3) including the exclusion region 211 and the region of interest ROI(15) including the exclusion region 212.

Note that, in the modification, similarly to the second modification of the first embodiment, the processing may be performed while moving the region of interest on a pixel-by-pixel basis or every several pixels.

In the modification, the region of interest may be set for individual observation target so that the optimal attenuation rate setting unit 611 does not include the extracted exclusion region.

Other Embodiments

The modes for carrying out the present invention have been described above, but the present invention is not limited only to the above-mentioned first and second embodiments. For example, the optimal attenuation rate setting unit may calculate values equivalent to the optimal attenuation rate which correspond to the optimal attenuation rate, in all frames of an ultrasound image, and may set, as the optimal attenuation rate, an average value, a median value, or a mode value of a predetermined number of the values equivalent to the optimal attenuation rate including a value equivalent to the optimal attenuation rate in the last frame. In this configuration, variation in optimal attenuation rate is reduced to have a stable value thereof, compared with the optimal attenuation rate set for each frame.

The optimal attenuation rate setting unit may set the optimal attenuation rate in every predetermined frames of an ultrasound image. Therefore, the calculation amount can be reduced. In this configuration, until a next optimal attenuation rate is set, a value of the last set optimal attenuation rate is preferably used.

The region of interest may be set for each sound ray or may be set as an area having a reception depth not less than a predetermined value. The input unit may receive these settings of the region of interest.

The input unit may receive input for changing settings of the initial value $\alpha_0$ of the attenuation rate candidate value.

As the statistical dispersion, for example, any of standard deviation, a difference between a maximum value and a minimum value of features in a population, and a half width of distribution of features may be applied. Note that, when an inverse variance is considered to be applied as the amount for the statistical dispersion, but, in this configuration, as a matter of course, an attenuation rate candidate value having a maximum value of the inverse variance is the optimal attenuation rate.

The statistical processing unit may calculate statistical dispersion for each of a plurality of kinds of corrected features, and set, as the optimal attenuation rate, an attenuation rate candidate value at which the calculated statistical dispersion is minimum.

The attenuation correction unit may perform the attenuation correction on the frequency spectrum using a plurality of attenuation rate candidate values, before performing the regression analysis on each frequency spectrum after the attenuation correction by the approximation unit to calculate the corrected feature.

In some embodiments, an ultrasound probe other than the ultrasound endoscope may be employed. For example, a miniature ultrasound probe having no optical system and having a small diameter may be adopted as the ultrasound probe. The miniature ultrasound probe is normally inserted into biliary tract, bile duct, pancreatic duct, trachea, bronchial tube, urethra, or urinary duct to be used for observation of nearby organs (pancreas, lung, prostate, bladder, lymph node, or the like). Further, as the ultrasound probe, an external ultrasound probe may be adopted to emit an ultrasound wave from a surface of the subject. The external ultrasound probe is normally used for observation of abdominal organs (liver, gallbladder, bladder), breast (in particular, mammary gland), or thyroid gland.

According to some embodiments, since an optimal attenuation rate is set to an observation target, and attenuation rate image data for indicating information on the optimal attenuation rate is generated, it is possible to provide image data including information on the attenuation rate which is set according to the observation target. Thus, even if tissue to be observed has an inhomogeneous structure, characteristics of the tissue can be accurately estimated based on ultrasound attenuation characteristics suitable for the observation target.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation apparatus comprising:
a central processing unit configured to:
analyze a frequency of an ultrasound signal to calculate a plurality of frequency spectra according to a reception depth and a reception direction of the ultrasound signal, wherein the ultrasound signal is obtained by an ultrasound probe comprising an ultrasound transducer configured to transmit an ultrasound wave to an observation target and to receive the ultrasound wave reflected from the observation target;
calculate uncorrected features of the plurality of frequency spectra in a region of interest that is one of a plurality of regions of interest, wherein the uncorrected features express attenuation of the ultrasound wave;

set a plurality of attenuation rate candidate values each of which provides a different attenuation characteristic in propagating the ultrasound wave through the observation target;

perform attenuation correction on the uncorrected features for eliminating influence of attenuation of the ultrasound wave, using each of the plurality of attenuation rate candidate values, to calculate corrected features of the plurality of frequency spectra for the region of interest;

calculate statistical dispersion of the corrected features for the region of interest;

set an attenuation rate from among the plurality of attenuation rate candidate values, having a minimum statistical dispersion as an optimal attenuation rate for the region of interest; and generate attenuation rate image data for the region of interest for displaying information on the optimal attenuation rate for the region of interest.

2. The ultrasound observation apparatus according to claim 1,
wherein the central processing unit is configured to generate the attenuation rate image data for the region of interest by adding visual information according to the optimal attenuation rate in the regions of interest.

3. The ultrasound observation apparatus according to claim 2,
wherein the plurality of regions of interest do not intersect one another, and
wherein the central processing unit is configured to add one set of visual information to each of the plurality of regions of interest.

4. The ultrasound observation apparatus according to claim 2,
wherein each of the plurality of regions of interest intersects at least another nearest region of interest, and
wherein the central processing unit is configured to add the visual information to a pixel at a predetermined position in each of the regions of interest.

5. The ultrasound observation apparatus according to claim 2,
wherein the central processing unit is configured to:
extract, as an exclusion region, a set of points where values of the corrected features calculated in the region of interest fall within a predetermined range; and
add, as the corrected features at the points in the exclusion region, a statistical value of the corrected features in a non-exclusion region in a corresponding region of interest, thereby to calculate the optimal attenuation rate.

6. The ultrasound observation apparatus according to claim 2,
wherein the central processing unit is configured to:
extract, as an exclusion region, a set of points where values of the corrected features calculated in each of the plurality of regions of interest fall within a predetermined range; and
add the visual information only to one or more of the plurality of regions of interest that do not contain the exclusion region extracted.

7. The ultrasound observation apparatus according to claim 1,
wherein the central processing unit is configured to calculate the uncorrected features of the plurality of frequency spectra in the region of interest by being configured to:
approximate each of the frequency spectra by an n-th order expression (n is a positive integer); and
calculate features of the n-th order expression as the uncorrected features.

8. The ultrasound observation apparatus according to claim 7,
wherein the central processing unit is configured to calculate the uncorrected features of the plurality of frequency spectra in the region of interest by being configured to:
approximate a predetermined frequency range in each of the frequency spectra by a linear expression; and
calculate one or more of an intercept and slope of the linear expression, and a mid-band fit that is a value of the linear expression at an intermediate frequency in the frequency range, as the uncorrected features.

9. A method comprising:
providing a central processing unit to perform:
analyzing a frequency of an ultrasound signal to calculate a plurality of frequency spectra according to a reception depth and a reception direction of the ultrasound signal, wherein the ultrasound signal is obtained by an ultrasound probe comprising an ultrasound transducer configured to transmit an ultrasound wave to an observation target and to receive the ultrasound wave reflected from the observation target;
calculating uncorrected features of the plurality of frequency spectra in a region of interest, wherein the uncorrected features express attenuation of the ultrasound wave;
setting a plurality of attenuation rate candidate values each of which provides a different attenuation characteristic in propagating the ultrasound wave through the observation target;
performing attenuation correction on the uncorrected features for eliminating influence of attenuation of the ultrasound wave, using each of the plurality of attenuation rate candidate values, to calculate corrected features of the plurality of frequency spectra for the region of interest;
calculating statistical dispersion of the corrected features for the region of interest:
setting an attenuation rate from among the plurality of attenuation rate candidate values, having a minimum statistical dispersion as an optimal attenuation rate for the region of interest; and
generating attenuation rate image data for the region of interest for displaying information on the optimal attenuation rate for the region of interest.

10. A non-transitory computer-readable recording medium with an executable program stored thereon, the program causing a computer to at least execute:
analyzing a frequency of an ultrasound signal to calculate a plurality of frequency spectra according to a reception depth and a reception direction of the ultrasound signal, wherein the ultrasound signal is obtained by an ultrasound probe comprising an ultrasound transducer configured to transmit an ultrasound wave to an observation target and to receive the ultrasound wave reflected from the observation target;

calculating uncorrected features of the plurality of frequency spectra in a region of interest, wherein the uncorrected features express attenuation of the ultrasound wave;

setting a plurality of attenuation rate candidate values each of which provides a different attenuation characteristic in propagating the ultrasound wave through the observation target;

performing attenuation correction on the uncorrected features for eliminating influence of attenuation of the ultrasound wave, using each of the plurality of attenuation rate candidate values, to calculate corrected features of the plurality of frequency spectra for the region of interest;

calculating statistical dispersion of the corrected features for the region of interest;

setting an attenuation rate from among the plurality of attenuation rate candidate values, having a minimum statistical dispersion as an optimal attenuation rate for the region of interest; and generating attenuation rate image data for the region of interest for displaying information on the optimal attenuation rate for the region of interest.

* * * * *